United States Patent
Shuman et al.

(10) Patent No.: US 12,102,377 B2
(45) Date of Patent: Oct. 1, 2024

(54) SLIDABLE COUPLING TO CONNECT DEVICES

(71) Applicant: Gyrus ACMI Inc., Southborough, MA (US)

(72) Inventors: Brandon J. Shuman, Kirkland, WA (US); Taylor N. Tyson, Seattle, WA (US); Eric Hadford, Maltby, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 259 days.

(21) Appl. No.: 17/115,958

(22) Filed: Dec. 9, 2020

(65) Prior Publication Data
US 2021/0169553 A1    Jun. 10, 2021

Related U.S. Application Data

(60) Provisional application No. 62/945,836, filed on Dec. 9, 2019, provisional application No. 62/945,825, filed
(Continued)

(51) Int. Cl.
*A61B 18/14*    (2006.01)
*A61B 17/00*    (2006.01)
(Continued)

(52) U.S. Cl.
CPC .......... *A61B 18/14* (2013.01); *A61B 18/1206* (2013.01); *A61B 18/1477* (2013.01);
(Continued)

(58) Field of Classification Search
CPC .......... A61B 18/14; A61B 2017/00477; A61B 2018/00196; A61B 2018/1467;
(Continued)

(56) References Cited

U.S. PATENT DOCUMENTS

| 4,574,783 A | 3/1986 | Kazuhiro et al. |
| 4,869,259 A | 9/1989 | Elkins |

(Continued)

FOREIGN PATENT DOCUMENTS

| CN | 113017820 A | 6/2021 |
| DE | 102020132423 A1 | 6/2021 |

(Continued)

OTHER PUBLICATIONS

Aug. 26, 2021, International Search Report issued for Application No. GB2019320.7.
(Continued)

*Primary Examiner* — Linda C Dvorak
*Assistant Examiner* — Abigail Bock
(74) *Attorney, Agent, or Firm* — Schwegman Lundberg & Woessner, P.A.

(57) ABSTRACT

Disclosed embodiments include apparatuses, systems, and methods for coupling devices. In an illustrative embodiment, an apparatus includes a locking body defining an opening with a first section having a first width and a second section having a second width smaller than the first width. The locking body is slidably mountable on a first device with a first coupling to receive a second coupling having a flange with a width that is smaller than the first width and larger than the second width. A slidable mounting mechanism slidably secures the locking body on the first device. The locking body slides between an open position, in which the first section is positionable to enable the first coupling to receive the second coupling, and a closed position in which an edge of the locking body around the second section abuts the flange to prevent withdrawal of the second coupling.

22 Claims, 18 Drawing Sheets

Related U.S. Application Data on Dec. 9, 2019, provisional application No. 62/945,843, filed on Dec. 9, 2019.

(51) Int. Cl.
*A61B 18/00* (2006.01)
*A61B 18/12* (2006.01)

(52) U.S. Cl.
CPC ............... *A61B 2017/00477* (2013.01); *A61B 2017/00526* (2013.01); *A61B 2017/00973* (2013.01); *A61B 2018/00077* (2013.01); *A61B 2018/00166* (2013.01); *A61B 2018/00178* (2013.01); *A61B 2018/00196* (2013.01); *A61B 2018/00202* (2013.01); *A61B 2018/00541* (2013.01); *A61B 2018/00577* (2013.01); *A61B 2018/00589* (2013.01); *A61B 2018/00744* (2013.01); *A61B 2018/1425* (2013.01); *A61B 2018/1435* (2013.01); *A61B 2018/144* (2013.01); *A61B 2018/1467* (2013.01); *A61B 2018/1475* (2013.01)

(58) Field of Classification Search
CPC . A61B 2017/00973; A61B 2018/00077; F16L 37/12; F16L 37/133
See application file for complete search history.

(56) References Cited

U.S. PATENT DOCUMENTS

| | | | |
|---|---|---|---|
| 5,919,202 A | 7/1999 | Yoon | |
| 5,935,102 A | 8/1999 | Bowden et al. | |
| 6,030,402 A | 2/2000 | Thompson et al. | |
| 6,416,510 B1 | 7/2002 | Altman et al. | |
| 6,749,604 B1 | 6/2004 | Eggers et al. | |
| 7,357,798 B2 | 4/2008 | Sharps et al. | |
| 7,419,488 B2 | 9/2008 | Ciarrocca et al. | |
| 8,043,286 B2 | 10/2011 | Palanker et al. | |
| 8,114,071 B2 | 2/2012 | Woloszko et al. | |
| 8,361,066 B2 | 1/2013 | Long et al. | |
| 9,539,012 B2 | 1/2017 | Landry et al. | |
| 9,888,926 B2 | 2/2018 | Phan et al. | |
| 10,987,161 B2 | 4/2021 | Shuman et al. | |
| 11,883,090 B2 | 1/2024 | Desmarais et al. | |
| 2002/0091382 A1 | 7/2002 | Hooven | |
| 2003/0028231 A1 | 2/2003 | Partridge et al. | |
| 2003/0083682 A1 | 5/2003 | Heise | |
| 2004/0059328 A1 | 3/2004 | Daniel et al. | |
| 2005/0021037 A1 | 1/2005 | McCombs et al. | |
| 2005/0096662 A1* | 5/2005 | Shores ................. | A61B 17/162 606/79 |
| 2005/0113827 A1 | 5/2005 | Dumbauld et al. | |
| 2009/0076412 A1 | 3/2009 | Rioux et al. | |
| 2009/0299362 A1 | 12/2009 | Long et al. | |
| 2010/0004723 A1 | 1/2010 | Foster et al. | |
| 2010/0256627 A1 | 10/2010 | Ma et al. | |
| 2010/0324637 A1 | 12/2010 | Trip et al. | |
| 2011/0213356 A1 | 9/2011 | Wright et al. | |
| 2012/0035474 A1 | 2/2012 | Deckman et al. | |
| 2012/0053485 A1 | 3/2012 | Bloom | |
| 2012/0143215 A1 | 6/2012 | Corrao et al. | |
| 2013/0190609 A1 | 7/2013 | Fischer, Jr. | |
| 2013/0204068 A1 | 8/2013 | Gnasashanmugam et al. | |
| 2013/0226026 A1 | 8/2013 | Dillard et al. | |
| 2013/0310823 A1 | 11/2013 | Gelfand et al. | |
| 2014/0051304 A1* | 2/2014 | Hoegerle ............ | A61B 17/1622 439/660 |
| 2014/0276764 A1 | 9/2014 | Shuman et al. | |
| 2014/0339821 A1* | 11/2014 | Ishizaka ................ | F16L 37/144 285/319 |
| 2015/0005769 A1 | 1/2015 | Klink et al. | |
| 2015/0105771 A1* | 4/2015 | Sim ..................... | A61B 18/1492 606/41 |
| 2016/0015451 A1 | 1/2016 | Shikhman | |
| 2018/0206903 A1 | 7/2018 | Podany | |
| 2018/0263681 A1* | 9/2018 | Shuman ............. | A61B 18/1492 |
| 2019/0167077 A1 | 6/2019 | Hancock et al. | |
| 2021/0169552 A1 | 6/2021 | Shuman et al. | |
| 2021/0169564 A1 | 6/2021 | Desmarais et al. | |

FOREIGN PATENT DOCUMENTS

| | | |
|---|---|---|
| EP | 1 870 051 A1 | 12/2007 |
| FR | 3104035 A1 | 6/2021 |
| GB | 2595016 A | 11/2021 |
| GB | 2595016 B | 12/2023 |
| JP | 2021090750 A | 6/2021 |

OTHER PUBLICATIONS

"U.S. Appl. No. 17/115,902, Non Final Office Action mailed Dec. 7, 2022", 15 pgs.

"U.S. Appl. No. 17/115,928, Response filed Jan. 3, 2023 to Restriction Requirement mailed Nov. 2, 2022", 7 pgs.

"U.S. Appl. No. 17/115,928, Restriction Requirement mailed Nov. 2, 2022", 5 pgs.

"French Application Serial No. 2012874, First Office Action mailed Apr. 29, 2021", with machine translation, 5 pgs.

"French Application Serial No. 2012874, Response filed Jun. 25, 2021 to First Office Action mailed Apr. 29, 2021", with English claims, 14 pgs.

"French Application Serial No. 2012874, Response filed Dec. 8, 2022 to Search Report mailed Aug. 8, 2022", with English claims, 18 pgs.

"French Application Serial No. 2012874, Search Report mailed Aug. 8, 2022", with machine translation, 24 pgs.

"U.S. Appl. No. 17/115,902, Examiner Interview Summary mailed Mar. 13, 2023", 2 pgs.

"U.S. Appl. No. 17/115,902, Response filed Apr. 3, 2023 to Non Final Office Action mailed Dec. 7, 2022", 9 pgs.

"U.S. Appl. No. 17/115,928, Examiner Interview Summary mailed Apr. 6, 2023", 2 pgs.

"U.S. Appl. No. 17/115,928, Non Final Office Action mailed Feb. 17, 2023", 11 pgs.

U.S. Appl. No. 17/115,902, filed Dec. 9, 2020, User Interface and Lock Features for Positioning Multiple Components Within a Body.

U.S. Appl. No. 17/115,928, filed Dec. 9, 2020, Helical Guide Channel With Variable Pitch.

"U.S. Appl. No. 17/115,902, Final Office Action mailed Feb. 20, 2024", 22 pgs.

"U.S. Appl. No. 17/115,902, Response filed Oct. 26, 2023 to Non Final Office Action mailed Jul. 27, 2023", 12 pgs.

"U.S. Appl. No. 17/115,928, Notice of Allowance mailed Sep. 20, 2023", 8 pgs.

"U.S. Appl. No. 17/115,928, Response filed Sep. 8, 2023 to Final Office Action mailed Jul. 20, 2023", 7 pgs.

"U.S. Appl. No. 17/115,902, Non Final Office Action mailed Jul. 27, 2023", 19 pgs.

"U.S. Appl. No. 17/115,928, Final Office Action mailed Jul. 20, 2023", 11 pgs.

"U.S. Appl. No. 17/115,928, Response filed May 16, 2023 to Non Final Office Action mailed Feb. 17, 2023", 9 pgs.

\* cited by examiner

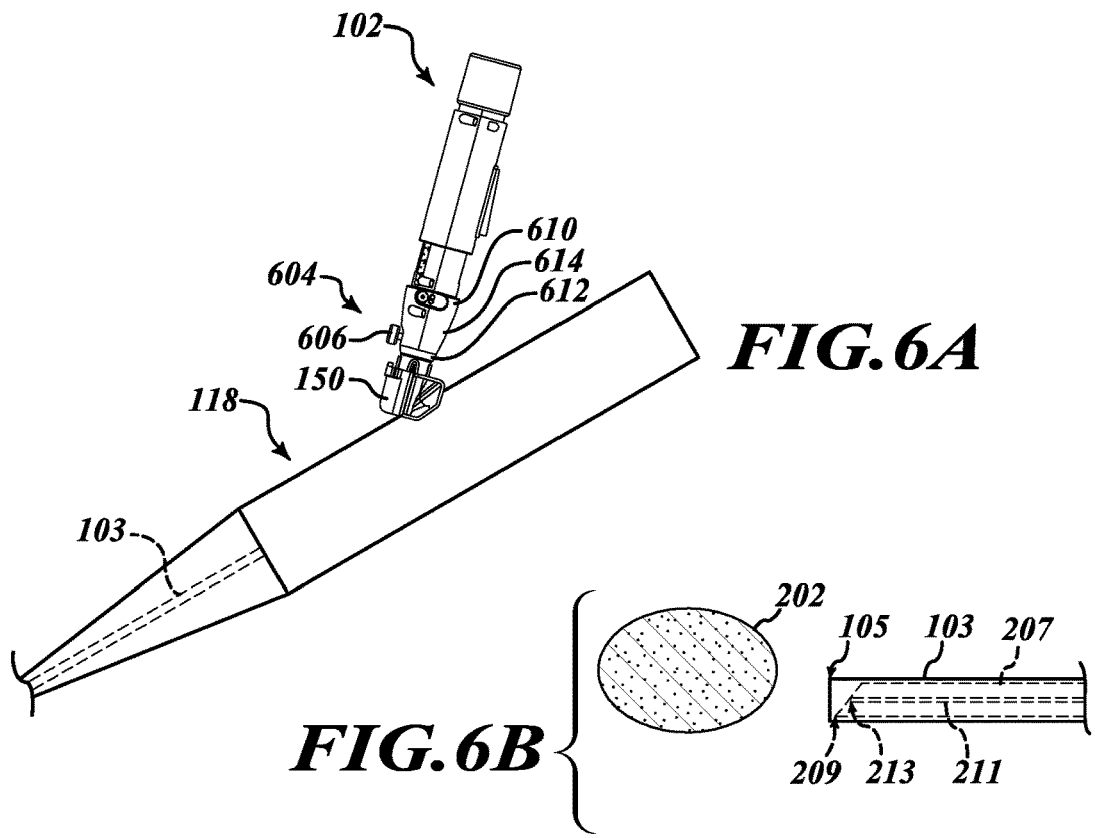
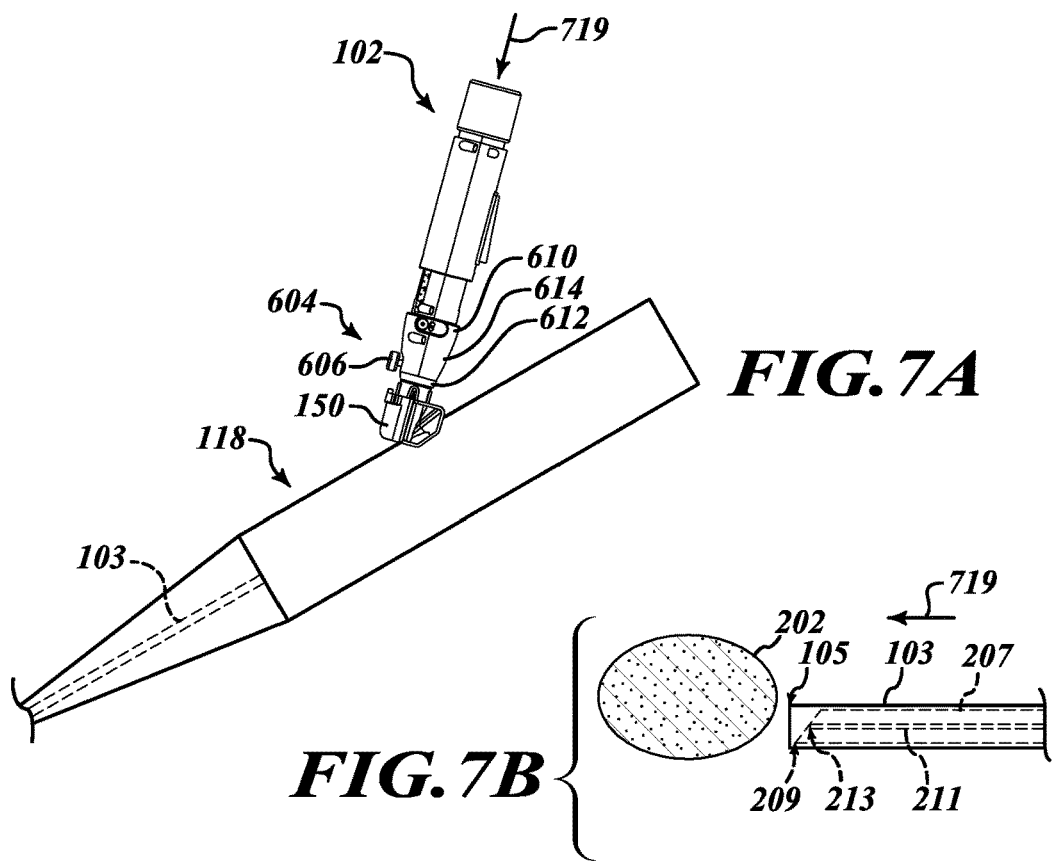

SLIDABLE COUPLING TO CONNECT DEVICES

PRIORITY CLAIM

The present application claims the priority and benefit of U.S. Provisional Patent Application Ser. No. 62/945,825 filed Dec. 9, 2019 and entitled "USER INTERFACE AND LOCK FEATURES FOR POSITIONING MULTIPLE COMPONENTS WITHIN A BODY," U.S. Provisional Patent Application Ser. No. 62/945,836 filed Dec. 9, 2019 and entitled "HELICAL GUIDE CHANNEL WITH VARIABLE PITCH," and U.S. Provisional Patent Application Ser. No. 62/945,843 filed Dec. 9, 2019 and entitled "SLIDABLE COUPLING TO CONNECT DEVICES."

FIELD

The present disclosure relates to a user interface and lock features for positioning multiple components within a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve inserting one or more electrodes through an orifice or a small incision and then extending the one or more electrodes to a desired location within a body of a patient. A radio frequency ("RF") electric current is then applied to the electrodes to coagulate, ablate, or otherwise treat tissue at that location. Monopolar electrosurgical instruments involve the insertion of one electrode that electrically interacts with a second electrode that is electrically connected to the body of the patient. A bipolar electrosurgical instrument involves the deploying of two electrodes at the location within the body of the patient where treatment is to be administered.

Positioning one or two electrodes at the desired location in a patient's body is an important part of electrosurgical treatments. Moving and holding electrodes in place, particularly when more than one electrode has to be moved or held independently of another electrode, may present a challenge for medical personnel directing the treatment. Further, because positioning one or more electrodes in place may involve following a particular sequence of steps in positioning the electrodes, assisting an operator in properly following the sequence also may be important.

SUMMARY

Disclosed embodiments include: apparatuses, systems, and methods for controlling the movement of multiple components within a body; apparatuses, systems, and methods for motivating elongated implements using a rotating actuator guided by a helical path of varying pitch; and apparatuses, systems, and methods for coupling a device, such as a user interface for controlling movement of multiple components within a body, to another device.

In an illustrative embodiment, an apparatus includes an elongated primary electrode defining a lumen therein, an elongated secondary electrode slidably receivable within the lumen, and a sheath configured to slidably receive the primary electrode therein, where the sheath is further configured to convey the primary electrode and the secondary electrode to a target region. A housing is operably coupled with the sheath and movably mounted to slidably motivate the sheath relative to the target region. A primary actuator is operably coupled with the primary electrode and slidably coupled with the housing to motivate the primary electrode relative to the sheath. A secondary actuator is operably coupled with the secondary electrode and movably coupled with the primary actuator to be slidable with the primary actuator to motivate the secondary electrode in concert with the primary electrode. The secondary actuator is rotatable independently of the primary actuator to travel along a helical path to motivate the secondary electrode to move relative to the target region independently of the primary electrode.

In another illustrative embodiment, a system for treating tissue at a target region includes an electrical power source configured to selectively provide electrical power between a first pole and a second pole via a two-pole electrical cable. An electrode control apparatus includes an elongated primary electrode defining a lumen therein, an elongated secondary electrode slidably receivable within the lumen, and a sheath configured to slidably receive the primary electrode therein, where the sheath is further configured to convey the primary electrode and the secondary electrode to a target region. A housing is operably coupled with the sheath and movably mounted to slidably motivate the sheath relative to the target region. A primary actuator is operably coupled with the primary electrode and slidably coupled with the housing to motivate the primary electrode relative to the sheath. A secondary actuator is operably coupled with the secondary electrode and movably coupled with the primary actuator to be slidable with the primary actuator to motivate the secondary electrode in concert with the primary electrode. The secondary actuator is rotatable independently of the primary actuator to travel along a helical path to motivate the secondary electrode to move relative to the target region independently of the primary electrode.

In a further illustrative embodiment, a method includes moving a distal end of a sheath that contains a primary electrode and a secondary electrode adjacent to a target region. A primary actuator operably coupled with the primary electrode and a secondary actuator operably coupled to the secondary electrode and movably engaged with the primary actuator are slid to a first position to motivate distal ends of the primary electrode and the secondary electrode relative to the target region. The secondary actuator is rotated relative to the primary actuator to cause the secondary actuator to travel independently of the primary actuator along a helical path to a second position to motivate the distal end of the secondary electrode to move independently of the primary electrode relative to the target region.

In an additional illustrative embodiment, an apparatus includes an elongated implement movable along an axis. A rotatable actuator is operably coupled with a proximal end of the implement to motivate the implement to move along the axis in response to rotation of the rotatable actuator. A guide is operably coupled with rotatable actuator, wherein the guide defines a generally helical path around the axis to direct movement of a rotatable actuator, and wherein a pitch of the helical path is varied to reduce a distance of travel of the actuator along the axis per unit of rotation of the actuator.

In another additional illustrative embodiment, a system includes an elongated primary electrode defining a lumen therein. An elongated secondary electrode is slidably receivable within the lumen. A sheath is configured to slidably receive the primary electrode therein, the sheath being further configured to convey the primary electrode and the secondary electrode toward a target region. A housing is operably coupled with the sheath and movably mounted to slidably motivate the sheath relative to the target region. A primary actuator is operably coupled with the primary electrode and slidably coupled with the housing to motivate the primary electrode to slide relative to the sheath along an axis. The primary actuator includes a guide defining a generally helical path, wherein a pitch of the helical path is varied to reduce movement of a guide member relative to the axis per unit of rotation of the guide member around the helical path. A secondary actuator is operably coupled with the secondary electrode and rotatably received within the guide of the primary actuator. The secondary actuator supports the guide member that is configured to engage the helical path. The secondary actuator is rotatable relative to the primary actuator to motivate the secondary electrode to move relative to the primary electrode.

In a further additional illustrative embodiment, a method includes coupling an elongated implement at a proximal end thereof to an actuator that is movable along an axis. The implement is motivated by rotatably moving the actuator through a generally helical path around the axis, where the helical path has a pitch that is varied to change a distance traveled by the actuator along the axis per unit of rotation of the actuator.

In another additional embodiment, a locking body defines an opening with a first section having a first width and a second section having a second width that is smaller than the first width, where the locking body is slidably mountable on one of a first device that supports a first coupling and a second device that supports a second coupling. One of the first and second couplings is configured to support thereon a flange having a flange width that is smaller than the first width and larger than the second width. A slidable mounting mechanism is configured to slidably secure the locking body on one of the first device and the second device. The slidable mounting mechanism is further configured to enable the locking body to slide between an open position, in which the first section is positionable to enable the first coupling to be inserted into the second coupling to form a connection, and a closed position, in which an edge of the locking body around the second section abuts the flange such that the coupling that supports the flange is prevented from being withdrawn from the connection In another additional illustrative embodiment, a system includes an elongated primary electrode defining a lumen therein. An elongated secondary electrode is slidably received within the lumen. A sheath slidably receives the primary electrode and is configured to convey the primary electrode and the secondary electrode toward a target region. A housing is operably coupled with the sheath and is movably mounted to slidably motivate the sheath relative to the target region. A primary actuator is operably coupled with the primary electrode and is movably coupled with the housing to motivate the primary electrode relative to the sheath. A secondary actuator is operably coupled with the second electrode and is movably coupled with the primary actuator, where the secondary actuator is separately movable relative to the primary actuator to motivate the secondary electrode to move relative to the primary electrode. A first coupling is supported by the housing and configured to engage a second coupling supporting a flange having a flange width, where the second coupling extends from a device through which the sheath and the electrodes will be conveyed to the target region. A locking body defines an opening having a first section having a first width larger than the flange width and a second section having a second width that is smaller than the flange width. A slidable mounting mechanism is configured to slidably secure the locking body to the housing. The slidable mounting mechanism is further configured to enable the locking body to slide between an open position, in which the first section is positionable to enable the first coupling to insertably receive the second coupling to form a connection, and a closed position, in which an edge of the locking body around the second section abuts the flange such that the coupling that supports the flange is prevented from being withdrawn from the connection.

In a further additional illustrative embodiment, a method includes positioning a locking body into an open position, where the locking body defines an opening with a first section having a first width and a second section having a second width that is smaller than the first width. The locking body is slidably mounted on one of a first device that supports a first coupling and a second device that supports a second coupling. The first section is disposed between the first coupling and the second coupling when the locking body is positioned into the open position. A connection is formed by inserting the first coupling within the second coupling such that one of the first and second couplings supports a flange having a flange width that is smaller than the first width and larger than the second width. The locking body is repositioned into a closed position in which an edge of the locking body around the second section abuts the flange to prevent the flange from being withdrawn from the connection.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 6A and 7A are schematic diagrams of moving a sheath actuator to position a sheath relative to the target region;

FIGS. 6B and 7B are schematic diagrams of distal ends of the sheath, a primary electrode, and a secondary electrode relative to the target region corresponding to positions of the sheath actuator of FIGS. 6A and 7A, respectively;

Figure 10:
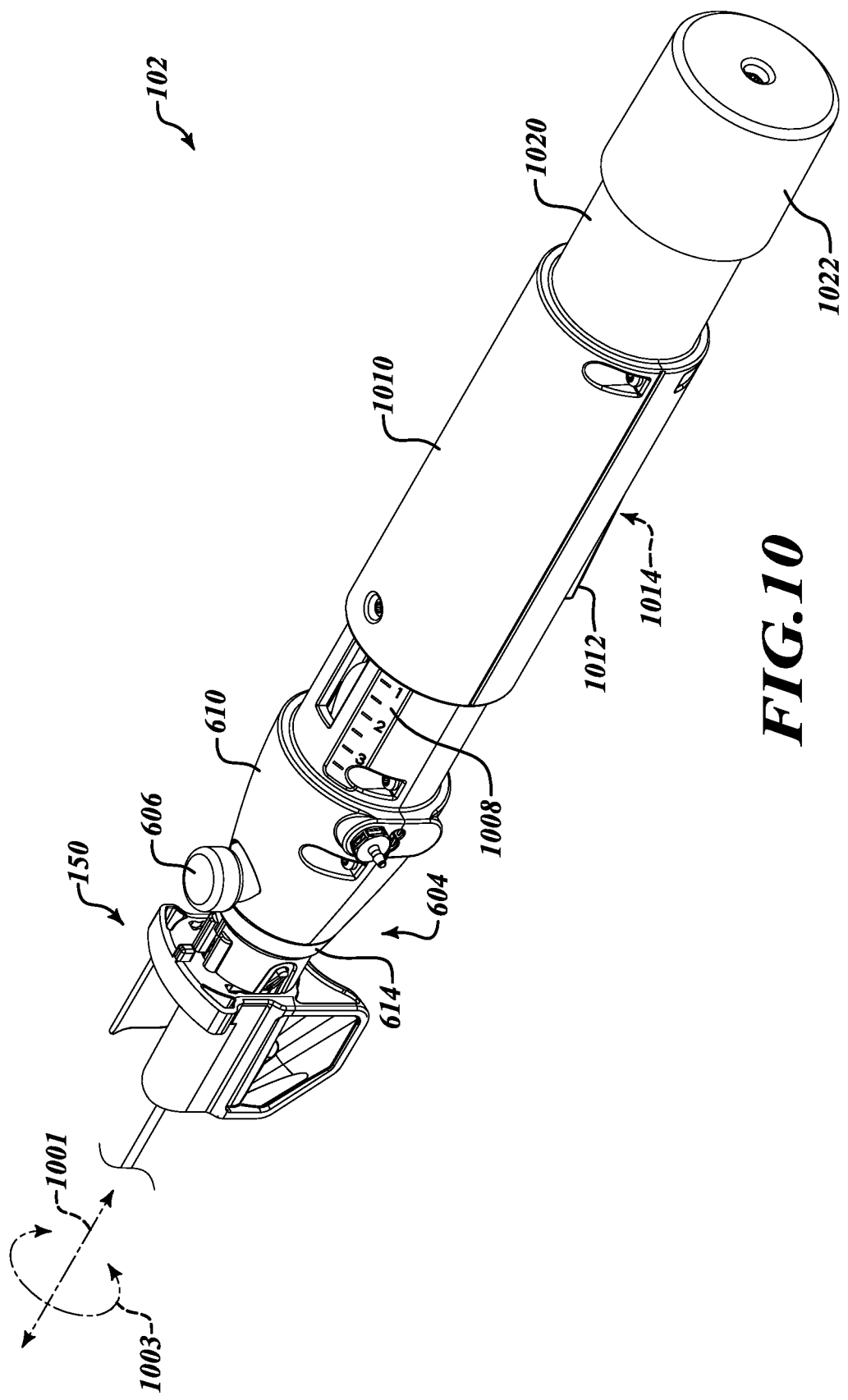
FIG. 10 is a side view of an embodiment of a user interface for positioning components relative to the target region.
Figure 22:
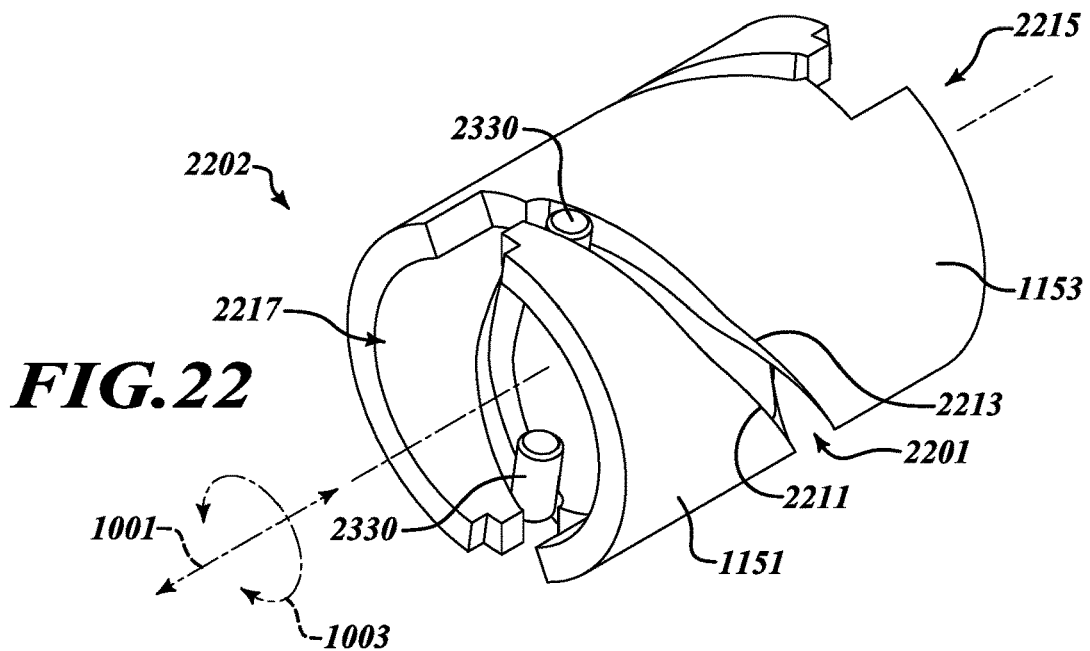
Figure 23:
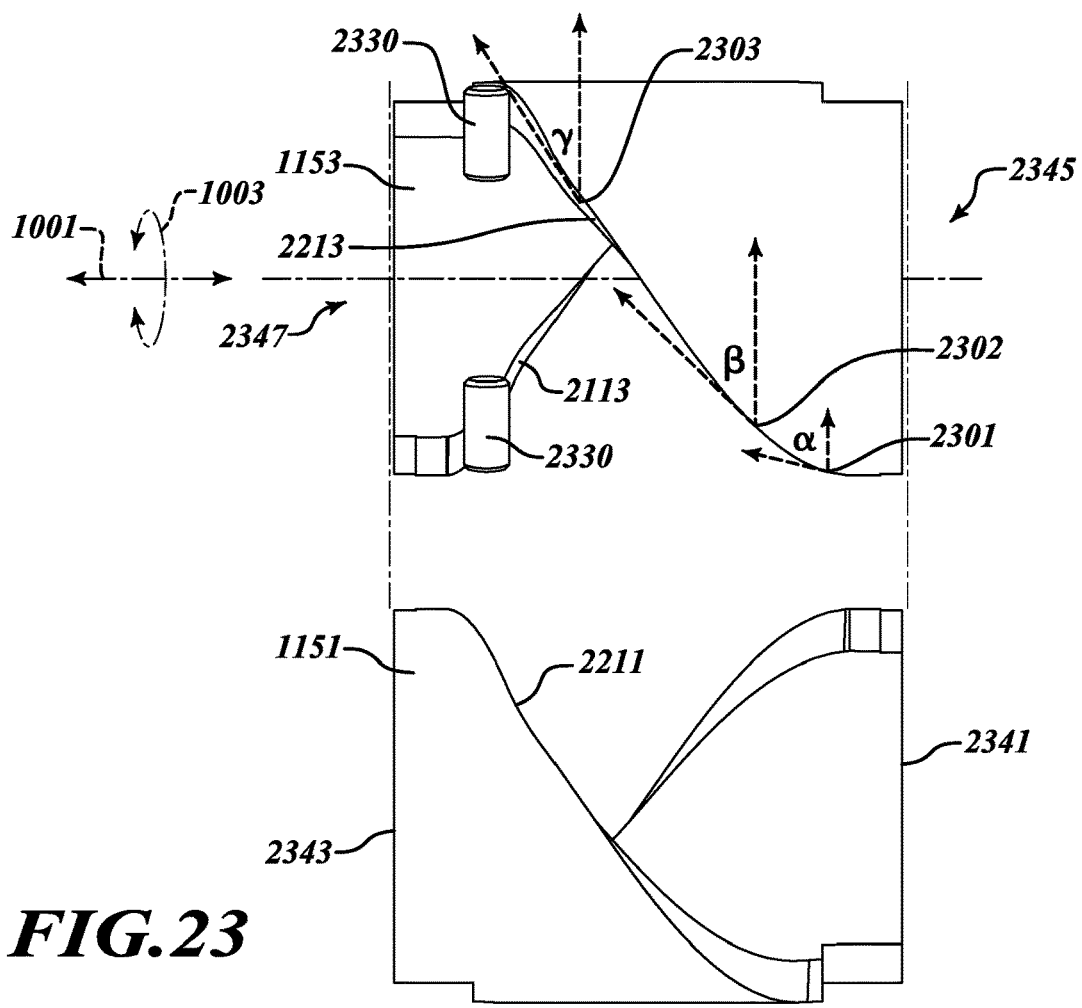
Figure 24:
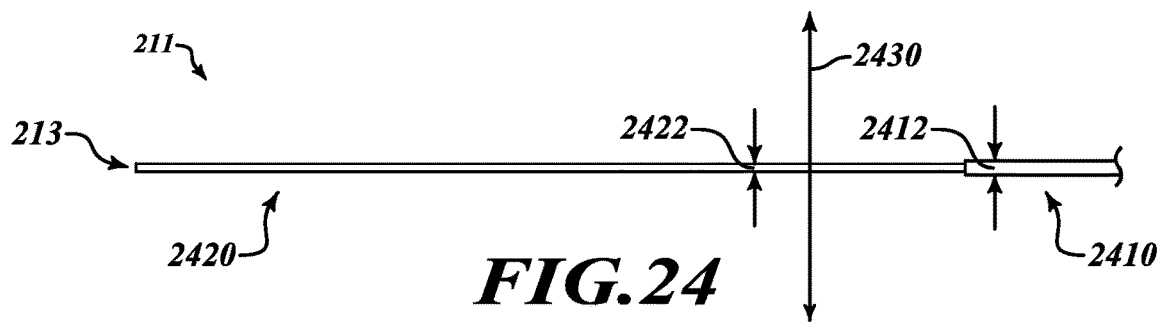
Figure 25:
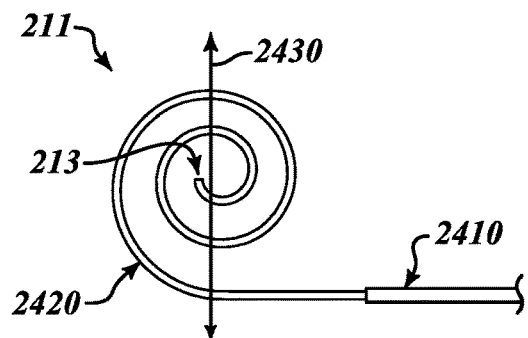
Figure 26:
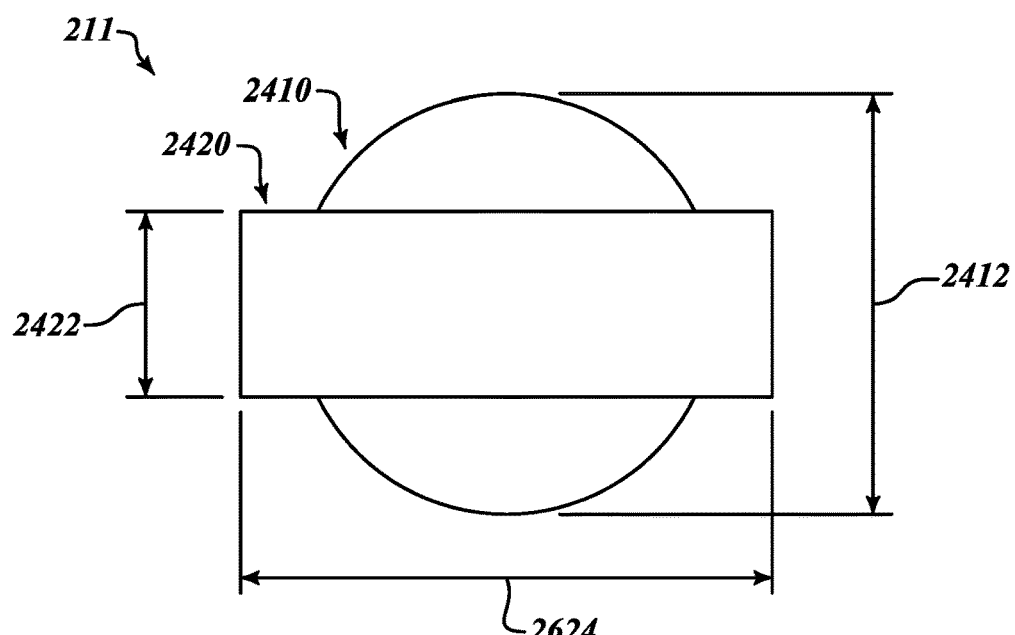
Figure 27:
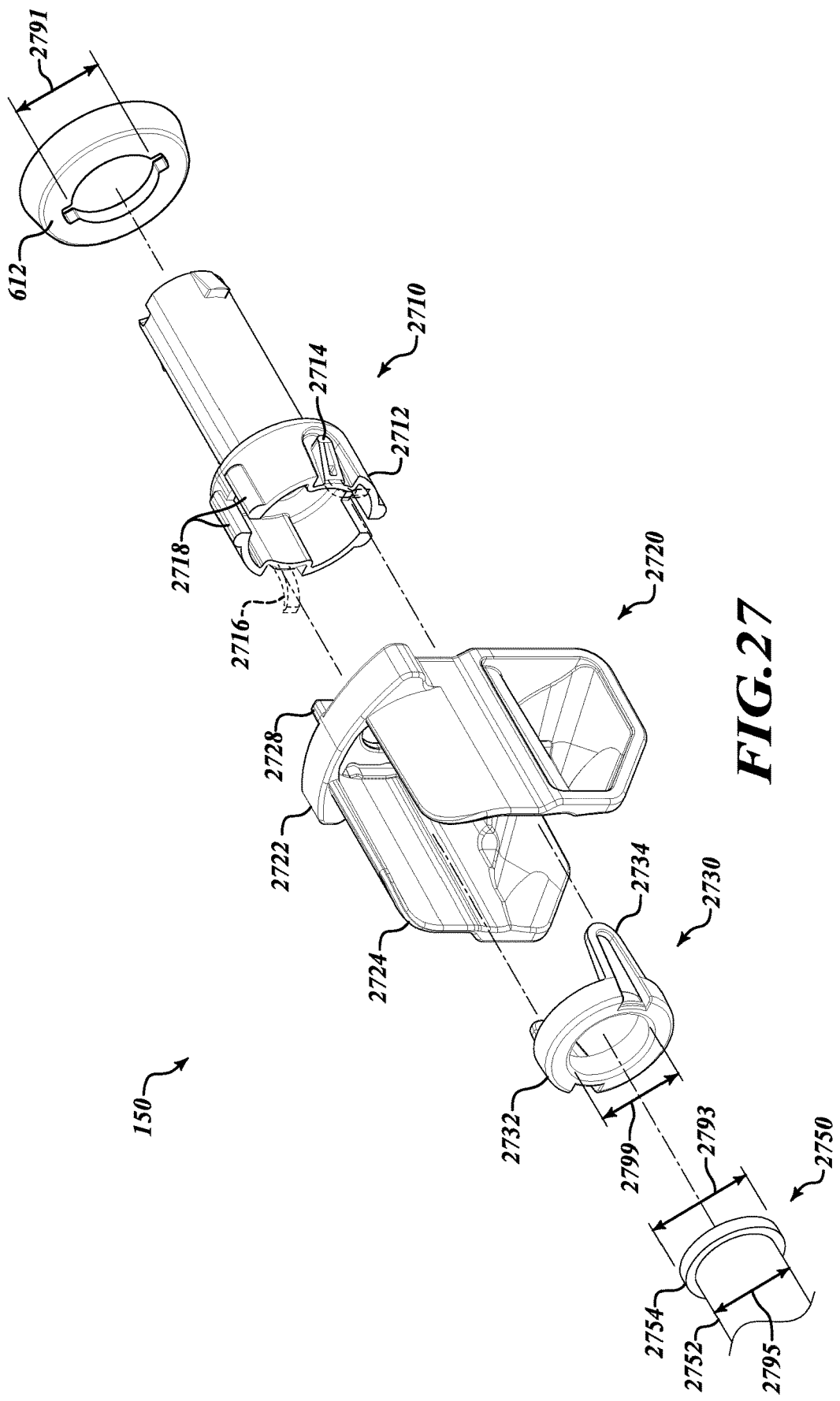
Figure 28:
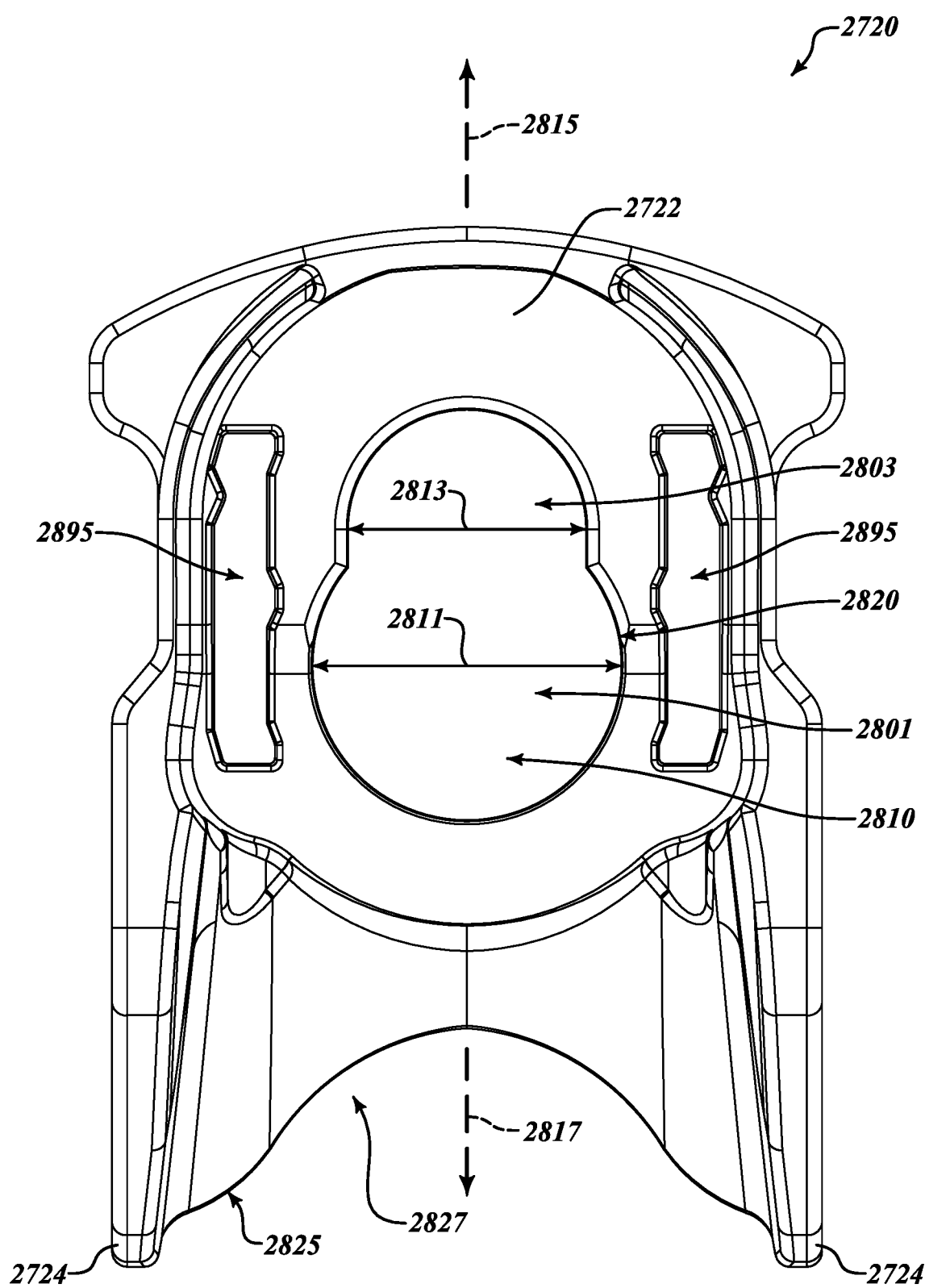
Figure 29:
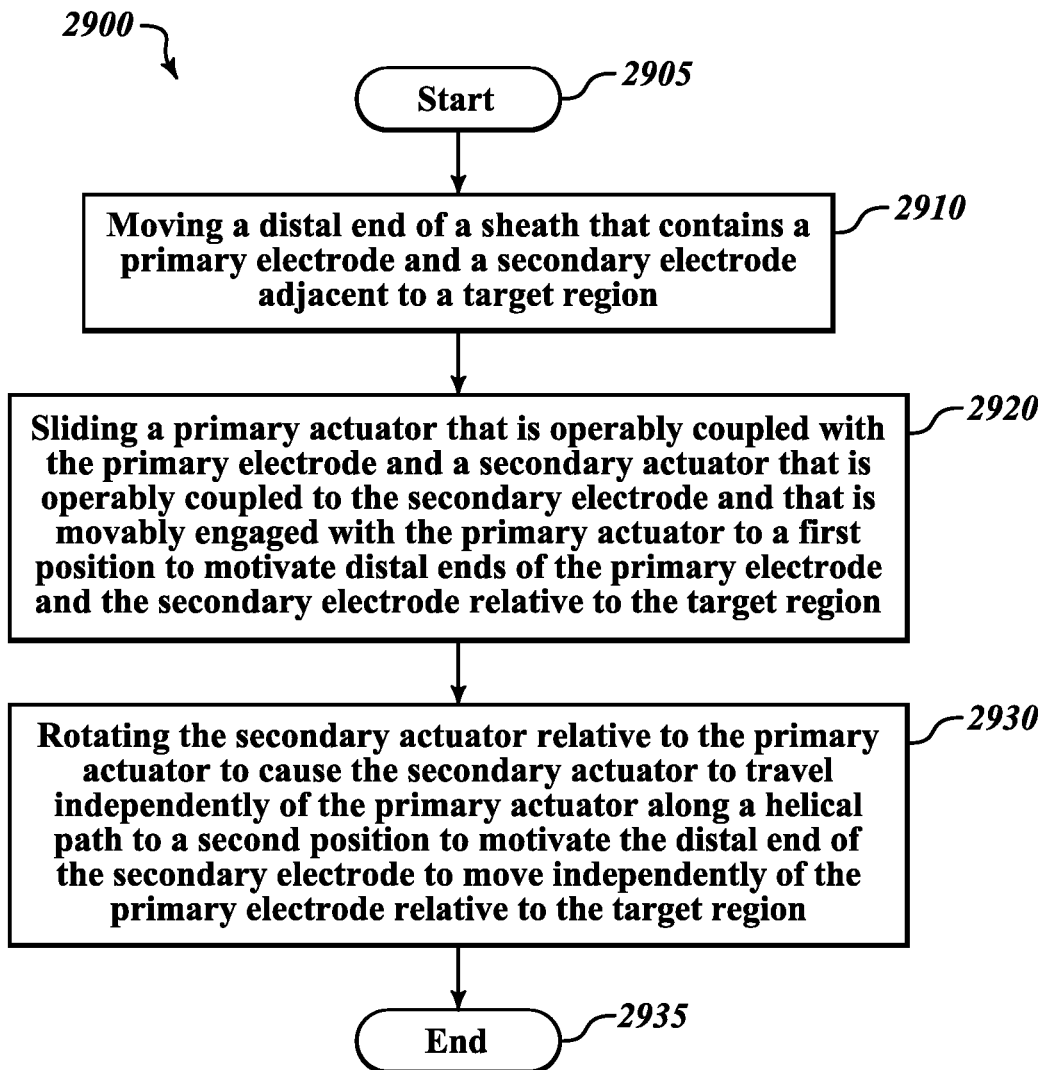
Figure 30:
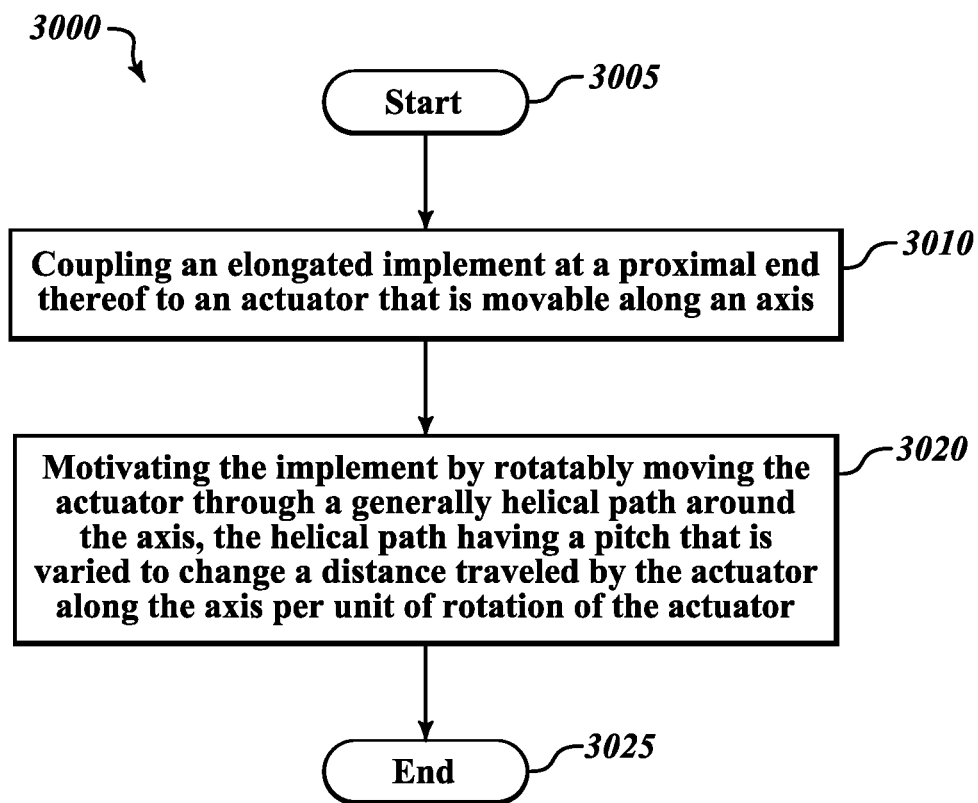
Figure 31:
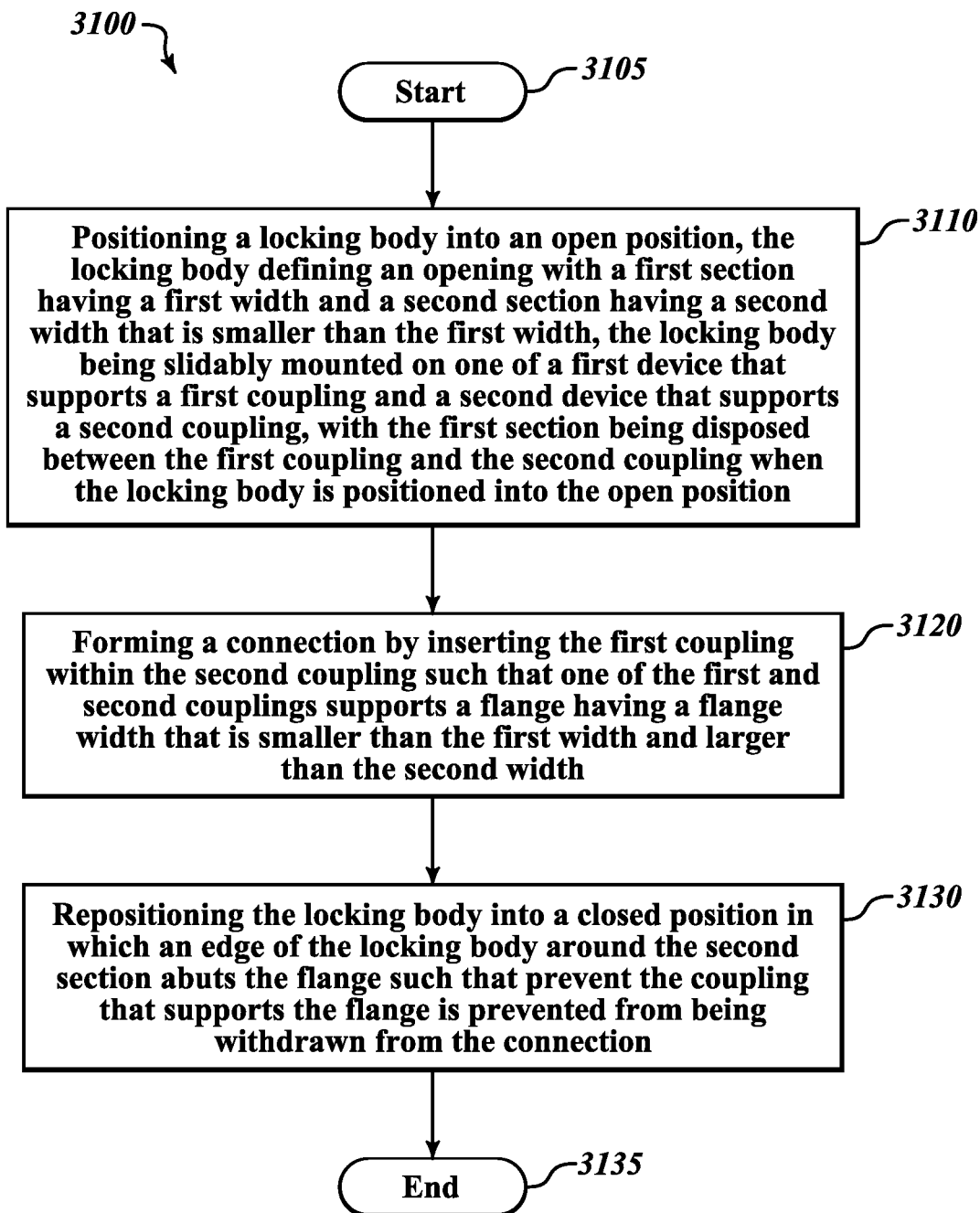

FIGS. 12A, 13A, 14A, 15A, 16A, 17A, 18A, 19A, 20A, and 21A are side views of an embodiment of the user interface of FIG. 10 being manipulated to position multiple components relative to the target region;

FIGS. 12B, 13B, 14B, 15B, 16B, 17B, 18B, 19B, 20B, and 21B are schematic diagrams of distal ends of the sheath, the primary electrode, and the secondary electrode relative to the target region corresponding to positions of the user interface of FIGS. 12A, 13A, 14A, 15A, 16A, 17A, 18A, 19A, 20A, and 21A, respectively;

FIG. 22 is a side view of a guide sleeve defining a helical channel of varying pitch for guiding a rotatable actuator;

FIG. 23 is a side view of sections of the guide sleeve of FIG. 22;

FIGS. 24 and 25 are side views of a wire having different cross-sections along its length;

FIG. 26 is a cross-sectional view of the wire of FIGS. 24 and 25;

FIG. 27 is an exploded view of a coupler for joining together devices;

FIG. 28 is a side view of a locking body of the coupler of FIG. 27;

FIG. 29 is a flow diagram of an illustrative method of positioning components using a user interface;

FIG. 30 is a flow diagram of an illustrative method of motivating an implement using a rotating actuator guided by a helical path of varying pitch; and FIG. 31 is a flow diagram of an illustrative method of coupling together devices with a slidably-mounted locking body.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two digits of two-digit figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes in a target region where electrical treatment, such as ablative treatment, is to be applied. For a specific example, the user interfaces and methods of their use may be used for ablating and/or coagulating tissue, removing lesions, and for performing other medical procedures within a lung.

It will be appreciated that various embodiments of user interfaces described herein may help to simplify the process of positioning the electrodes and holding the electrodes in place. As will be described below, various embodiments of the user interface accomplish the selective positioning and locking in place of the electrodes by depressing a release, sliding one actuator, and rotating another.

Figure 1:
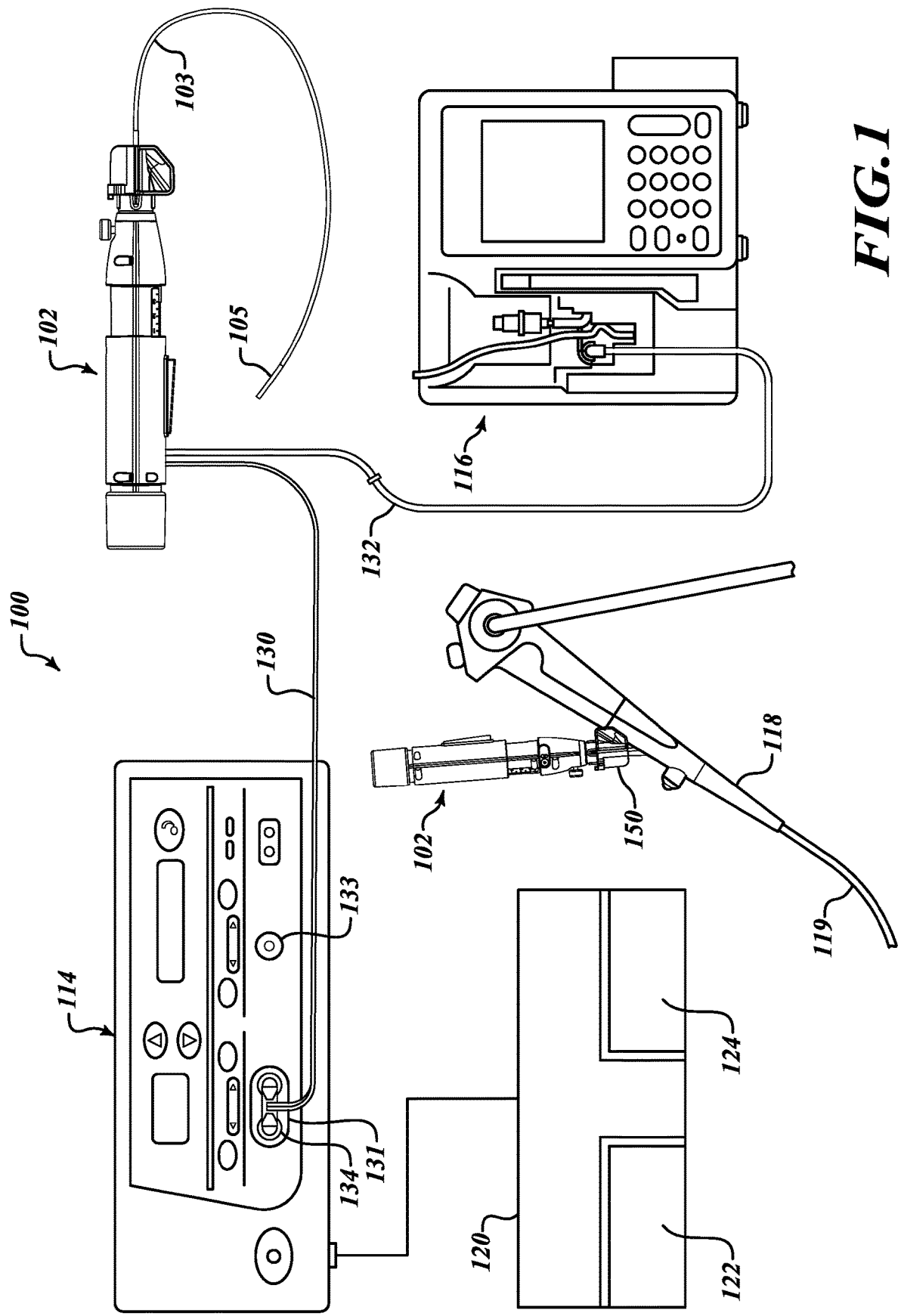
FIG. 1 is a block diagram in partial schematic form of an illustrative system for treating tissue.

Referring to FIG. 1, a system 100 is provided for treating tissue at a target region of a patient (not shown in FIG. 1). The system 100 may be a bipolar or monopolar radio frequency (RF) system, as desired, for treating tissue in a patient. However, various embodiments described herein are configured to position two electrodes at the target region to support implementation of a bipolar treatment system, thereby allowing for electric current to be selectively passed through a particular target region in a patient. Specifically, the system 100 may be employed for coagulation and/or ablation of soft tissue during percutaneous and/or endoscopic surgical procedures, such as, for example, bronchoscopic surgical procedures for partial and/or complete ablation of cancerous and/or noncancerous organ lesions. As will be further described, the tissue is treated by positioning one or more electrodes proximate the tissue to be treated and passing an electrical current through the tissue.

In some embodiments, the system 100 includes a user interface 102, an electrosurgical radio frequency (RF) generator operating as a switchable current source 114, an infusion pump 116, and an electrosurgical instrument or device 118, such as, without limitation, a bronchoscope or any other electrosurgical or endoscopic instrument as desired for a particular application. The user interface 102 may be joined with the electrosurgical apparatus 118 with a coupler 150. The electrosurgical apparatus 118 may be used to convey electrodes (not shown in FIG. 1) through a sheath 103 where the user interface 102 may be used to manipulate positions of the electrodes at the target region.

The user interface 102 electrically communicates with the switchable current source 114 though an electrical conductor 130. In some embodiments, the electrical conductor 130 is connected to a bipolar outlet 131 on the switchable current source 114 when the system is operated in a bipolar mode. The electrical conductor 130 may be coupled with the outlet 131 using an electrical connector 134 configured to electrically engage the outlet 131. The electrical conductor 130 may be removably or fixably coupled to the user interface 102, where a flexible electrical coupling (not shown in FIG. 1) associated with the user interface 102 electrically couples the current to the electrodes, as further described below with reference to FIG. 11. In some other embodiments, the system 100 can be operated in a monopolar mode when the electrical conductor 130 is connected to a secondary outlet 133 with an adapter (not shown in FIG. 1).

The user interface 102 is further connected to the infusion pump 116 with a tube 132 that facilitates the flow of a conductive fluid, such as saline solution, from the infusion pump 116 to the user interface 101. As also described below with reference to FIG. 11, the user interface 102 may include a flexible fluid coupling (not shown in FIG. 1) that receives the flow of conductive fluid from the infusion pump 116 and delivers the conductive fluid to an interior of a primary electrode where it can be delivered to the target region.

The switchable current source 114 may be operated with the use of a foot operated unit 120 electrically connected to the switchable current source 114. The foot operated unit 120 may include a pedal 122 that directs the switchable current source 114 to apply an electrical current to one or more electrodes to cut, ablate, or otherwise treat tissue and a pedal 124 that instructs the switchable current source 114 to apply a lower electrical current to the one or more electrodes to coagulate tissue.

In various embodiments the electrosurgical apparatus 118 includes an insertion tube 119 that permits insertion of the sheath 103 into a body (not shown) through an orifice or an incision. A distal end 105 of the sheath 103 is delivered to a target region where treatment is to be administered. The sheath 103 contains and conveys the electrodes (not shown) to a desired treatment location. Positioning of the distal end 105 of the sheath 103 and the distal ends of the electrodes (not shown in FIG. 1) may be controlled by the user interface 102 received by the electrosurgical apparatus 118 as further described below with reference to FIGS. 6A-21B.

Referring to FIGS. 2-5, distal ends of components used to administer treatment are positioned relative to a target region 202 using various embodiments of a user interface 102. The target region 202, may include a lesion or any portion of tissue to be treated within a body. Various embodiments of the user interface 102 described below are capable of positioning the components as described with reference to FIGS. 2-5 and as further described with reference to FIGS. 6A-21B. The description of FIGS. 2-5 is provided as a baseline to describe an application with which various embodiments of the user interface 102 may be used to deploy these components.

In various embodiments, a secondary electrode 211 is slidably received within a primary electrode 207, and the primary electrode 207 is slidably received within a sheath 203. Components contained within other components are represented with dashed lines in FIGS. 2-5. In various embodiments, the primary electrode 207 is in the form of a needle, with the distal end 209 being configured to pierce tissue, such as tissue comprising the target region 202. Piercing the tissue at the target region 202 with the primary electrode facilitates positioning the distal end 209 of the primary electrode 207 at a desired position and also facilitates conveying the secondary electrode 211 to a desired location. In various embodiments, until a user interface is manipulated to separately move the secondary electrode 211, the primary electrode 207 and the secondary electrode 211 move in concert, at a same time and through a same distance, with each other and with the sheath 203.

Figure 2:
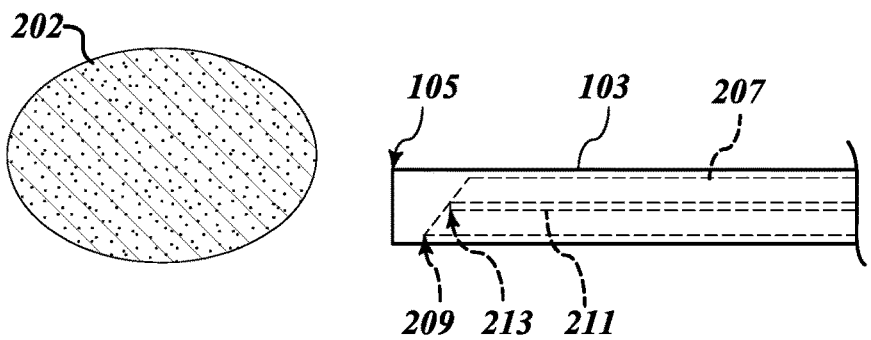
FIGS. 2-5 are schematic diagrams of positioning of distal ends of a sheath, primary electrode, and secondary electrode relative to a target region.

Referring to FIG. 2, the sheath 103, the primary electrode 207, and the secondary electrode 211 are positioned at an initial position near the target region 202. The sheath 103 and the electrodes 207 and 211 received therein may be conveyed to this location through the use of a bronchoscope or other electrosurgical device 118, as previously described with reference to FIG. 1. A distal end 105 of the sheath 103 is positioned in the vicinity of the target region 202. The primary electrode 207 is slidably received within the sheath 103, with a distal end 209 of the primary electrode 207 at or near the distal end 105 of the sheath 103. Specifically, FIG. 2, for example, shows the distal end 209 of the primary electrode 207 positioned just short of the distal end 105 of the sheath 103. In turn, the secondary electrode 211 is slidably received within the primary electrode 207, with the distal end 213 of the secondary electrode 211 positioned just within the distal end 209 of the primary electrode 207.

Figure 3:
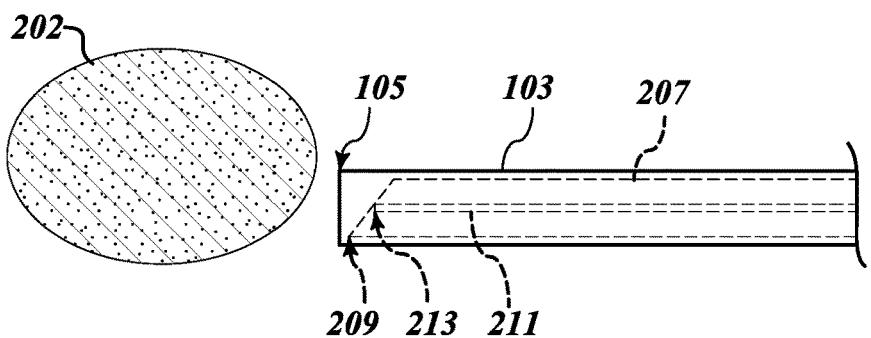

Referring to FIG. 3, the sheath 103, the primary electrode 207, and the secondary electrode 211 are positioned once the sheath 103 has been moved closer to the target region 202. The sheath 103 may be moved toward the target region 202 using a sheath actuator, as described below with reference to FIGS. 6A-7B. As contrasted with FIG. 2, in FIG. 3, the distal end 105 of the sheath 103 has been moved closer to the target region 202. Because the primary electrode 207 and the secondary electrode 211 have not been separately moved through the manipulation of a user interface (not shown), the primary electrode 207 and the secondary electrode 211 have moved in concert with the sheath 103, traveling a same distance in a same direction as the sheath 103. The distal end 209 of the primary electrode 207 remains positioned just short of the distal end 105 of the sheath 103, and the distal end 213 of the secondary electrode 211 remains positioned just within the distal end 209 of the primary electrode 207.

Figure 4:
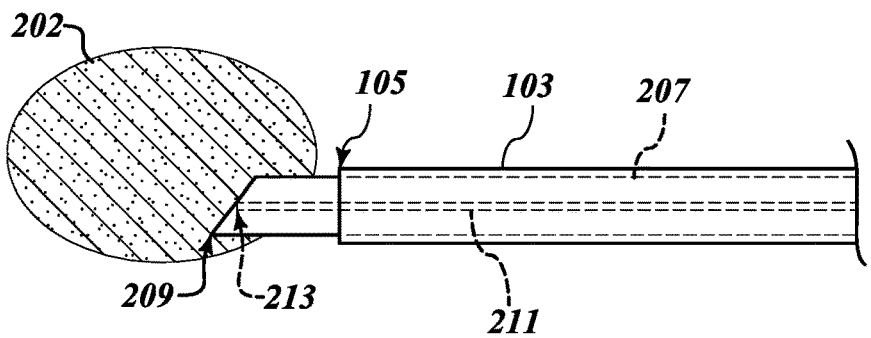

Referring to FIG. 4, the sheath 103, the primary electrode 207, and the secondary electrode 211 are positioned once the primary electrode 207 has been extended from the sheath 103 into the target region 202. In various embodiments, the secondary electrode 211 moves in concert with the primary electrode 207 as the primary electrode 207 is extended beyond the distal end 105 of the sheath 103. Thus, the secondary electrode 211 moves in the same direction and moves through the same distance as the primary electrode 207, as shown in FIG. 4. The distal end 213 of the secondary electrode 211 remains positioned just within the distal end 209 of the primary electrode 207.

Figure 5:
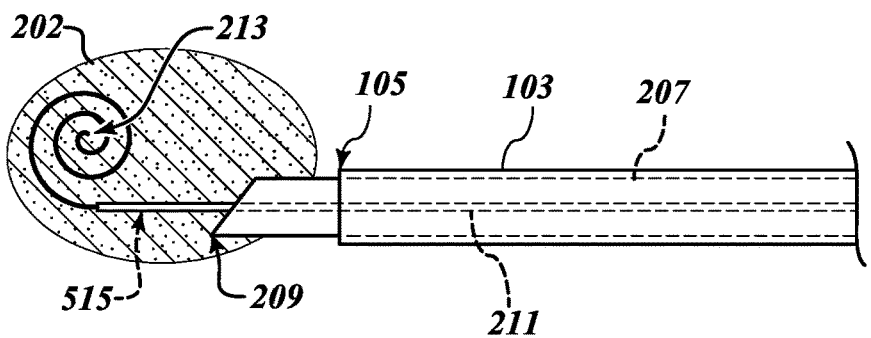

Referring to FIG. 5, the sheath 103, the primary electrode 207, and the secondary electrode 211 are positioned once the secondary electrode 211 has been extended from the primary electrode 207. A distal end 213 of the secondary electrode 211 is deployed at a position across the target region 202 from the primary electrode 207. In particular embodiments, the secondary electrode 211 is configured as a coilable wire which is constrained within the primary electrode 207 in a straightened form. The secondary electrode 211 may be formed of an alloy, such as nitinol, a nickel-titanium allow, or other "memory" alloy to regain a certain shape after being released from a confined position. Once the user interface 102 (not shown in FIG. 5) is manipulated to independently extend the secondary electrode 211 from the primary electrode 207, a portion of the secondary electrode 211 coils. As a result, the distal end 213 of the secondary electrode 211 augers into tissue at the target region 202. The augering of the distal end 213 of the secondary electrode 211 may assist in securing the position of the distal end 213 of the secondary electrode 211 during treatment.

Still referring to FIG. 5, an insulated section 515 of the secondary electrode 211 stops short of the distal end 213 of the secondary electrode 211. The insulation 515 electrically insulates the secondary electrode 211 from the primary electrode 207 such that, when electrical current is applied to proximal ends (not shown) of the primary electrode 207 and the secondary electrode 211, the electrical current may only flow between the distal end 209 of the primary electrode 207 and the uninsulated distal end 213 of the secondary electrode 211.

As will be further described below, various embodiments of the user interface 102 facilitate moving the primary electrode 207 and the secondary electrode 211 in concert with the sheath 103 as the sheath is positioned adjacent the target region 202, as described with reference to FIG. 3. Various embodiments of the user interface also facilitate moving the primary electrode 207 and the secondary electrode 211 in concert as they are extended beyond the distal end 105 of the sheath 103, as described with reference to FIG. 4. To this end, various embodiments of the user interface 102 may prevent moving the secondary electrode 211 independently of the primary electrode 207 until the primary electrode 207 is extended beyond the distal end 105 of the sheath 103. Once the primary electrode 207 has been extended, various embodiments of the user interface facilitate moving the secondary electrode 211 independently of the primary electrode 207 to permit separate positioning of the secondary electrode, as described with reference to FIG. 5. Further, once the primary electrode 207 is deployed at a desirable position, various embodiments of the user interface may prevent the primary electrode 207 from being moved while the secondary electrode 211 is being separately deployed and/or once the secondary electrode 211 has been situated at a desired location. Embodiments of a user interface 102 to coordinate movements of the sheath 103 and electrodes 207 and 211 is explained below with reference to FIGS. 6A-20.

Referring to FIGS. 6A and 6B, the user interface 102 includes a sheath actuator 604 that is used to position the distal end 105 of the sheath 103, as previously described with reference to FIG. 3. The user interface 102 is joined with the electrosurgical apparatus 118 with the coupler 150, as previously described with reference to FIG. 1. The electrosurgical apparatus 118, such as a bronchoscope or another minimally invasive device used for performing diagnostic or therapeutic tasks, conveys the sheath 103 into the body (not shown in FIGS. 6A and 6B) near the target region 202.

Again referring to FIG. 6A, the user interface 102 includes a sheath actuator 604 and a sheath lock 606 configured to move the sheath 103 to position the distal end 105 of the sheath 103 at a desired location relative to a target region 202. In some embodiments, the sheath actuator 604 may be a slidable mechanism incorporating a slidable sleeve 612. At one end, the slidable sleeve 612 is slidably received within a collar 614 at an end of a housing 610 of the user interface 102. At an opposing end, the slidable sleeve 612 is joined with the coupler 150. The slidable sleeve 612 may be locked in position at the collar 614 by the sheath lock 606. The sheath lock 606 may include a thumbscrew, a spring-loaded locking pin, or another mechanism configured to mechanically engage the slidable sleeve 612 to secure the slidable sleeve 612—and, in turn, the sheath 103—in place at a desired location. In some other embodiments, the sheath actuator 604 may, for example, be part of the electrosurgical apparatus 118. Any such embodiments of the sheath actuator 604 may facilitate movement of the sheath 103, as further described below.

Referring to FIG. 6B, before engaging the sheath actuator 604 to extend the sheath 103, the sheath 103 and the primary electrode 207 and the secondary electrode 211 received therein are positioned near the target region 202, as shown in FIG. 2.

Referring to FIGS. 7A and 7B, manipulation of the sheath actuator 604 illustrates an example of how the sheath 103 may be unlocked and moved into position as previously described with reference to FIG. 3. In the configuration shown in FIGS. 7A and 7B, the sheath actuator 604 has been manipulated to enable the sheath 103 to be moved a distance 719 closer to the target region 202. Specifically, the sheath lock 606 of the sheath actuator 604 is released to enable movement of the slidable sleeve 612 within the collar 614. Then, the housing 610 of the user interface 102 is moved a distance 719 relative to the electrosurgical device 118 to move the sheath 103 the same distance 719 toward the target region 702. Once the distal end 105 of the sheath 103 has reached the desired location relative to the target region 202, the slidable sleeve 612 may be locked in position at the collar 614 by the sheath lock 606. In various embodiments of the user interface 102, the electrodes 207 and 211 move with the housing 610, so that when the housing 610 is moved to reposition the sheath 103, the electrodes 207 and 211 move in concert with the sheath 103. Therefore, as shown in FIG. 7B, while the distal end 105 of the sheath 103 is advanced toward the target region 202, the electrodes 207 and 211 move with the sheath 203. As in FIG. 6B, the distal end 209 of the primary electrode 207 remains within the distal end 105 of the sheath 103 and the distal end 213 of the secondary electrode 211 remains within the distal end 209 of the primary electrode 207.

Figure 8:
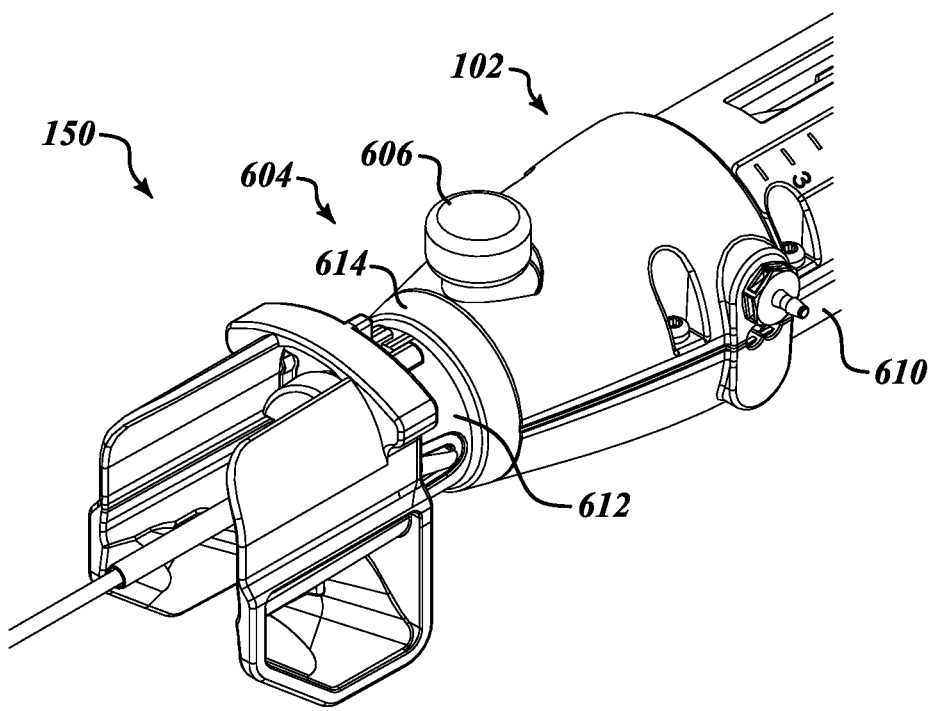
FIG. 8 is a side view of an illustrative sheath actuator and a sheath lock.

Referring to FIG. 8, in an illustrative sheath actuator 604 and a sheath lock 606 the slidable sleeve 612 is slidably received within the collar 614 of the housing 610. The slidable sleeve 612 is fixably attached to the coupler 150 that engages the user interface 102 with the electrosurgical apparatus (not shown in FIG. 8). The sheath lock 606 in the embodiment of FIG. 8 is a thumbscrew that may be loosened to permit movement of the collar 614 fixably attached to the coupler 150 to move the sheath (not shown in FIG. 8) as previously described with reference to FIGS. 6A-7B. After the housing 610 has been manipulated to slide the collar 614 relative to the slidable sleeve 612 to move the distal end 105 of the sheath 103 to a desired location, such as described with reference to FIG. 7B, the sheath lock 606 is reengaged, such as by turning a thumbscrew, to fix the position of the sheath.

Figure 9:
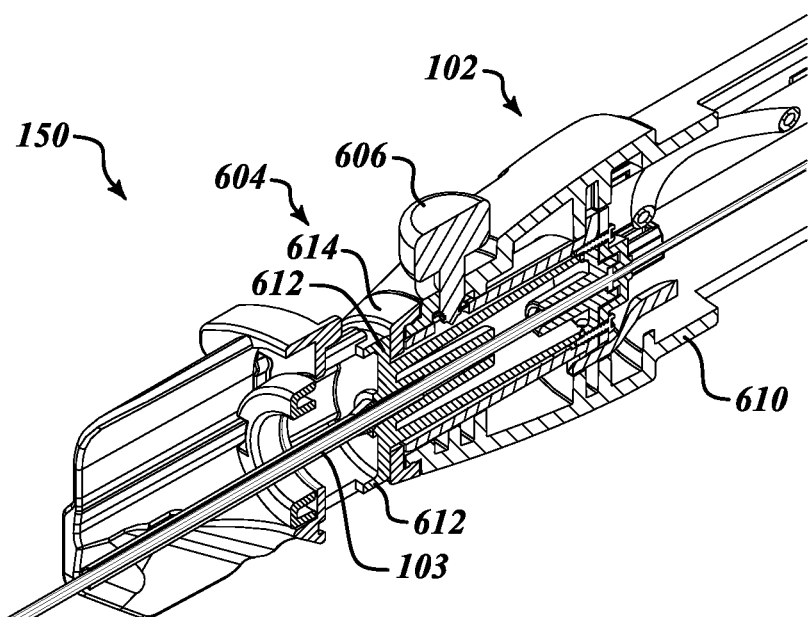
FIG. 9 is a cutaway view of the sheath actuator and sheath lock of FIG. 8.

Referring to FIG. 9, the sheath 103 and the electrodes 207 and 211 extend through the slidable sleeve 612. As a result, movement of the housing 610, to which the sheath 103 and the electrodes 207 and 211 are operably coupled, results in movement of the sheath 103 and the electrodes 207 and 211. A distal end 907 of the sheath lock 606 that extends through the collar 614 mechanically engages the slidable sleeve 612 to control movement of the slidable sleeve 612. Releasing the sheath lock 606, such as by loosening a thumb screw, permits the slidable sleeve 612 to be slidably moved relative to the collar 614 by moving the housing 610, as described with reference to FIG. 7A. Securing the sheath lock 606, such as by tightening the thumbscrew, mechanically secures the slidable sleeve 612 in place relative to the collar 614, preventing further movement of the slidable sleeve 612, thereby securing the distal end 105 of the sheath 103 in place.

Referring to FIG. 10, in various embodiments, the user interface 102 includes control surfaces for positioning the sheath 103 and the electrodes 207 and 211 (none of which are shown in FIG. 10). The user interface 102 includes the housing 610 that supports components that are moved parallel along an axis 1001 or that are rotated along a curve 1003 around the axis 1001, as further described below. The user interface 102 includes the sheath actuator 604, including the collar 614 that receives the slidable sleeve 612 (fully received within the collar 614 and, thus, not shown in FIG. 10) and the sheath lock 606. The sheath actuator 604 joins the housing 610 to the coupler 150 which, in turn, couples the user interface 102 with an electrosurgical device (not shown in FIG. 10). As further described in more detail below, the user interface 102 includes a primary actuator 1010, which controls movement of the primary electrode 207 (not shown in FIG. 10), and a secondary actuator 1020, which controls movement of the secondary electrode 211 (not shown in FIG. 10).

The primary actuator 1010 includes a depressible actuator lock 1012 that extends through an actuator opening 1014 in the primary actuator 1010. The primary actuator 1010 is slidably engaged with the housing 610. The actuator lock 1012 is hingeably or flexibly mounted on the primary actuator 1010. Depressing the actuator lock 1012 partially moves the actuator lock 1012 through the actuator opening 1014 and a corresponding opening or recess (not shown in FIG. 10) in the housing 610 to disengage the primary actuator 1010 from the housing 610. As a result, depressing the actuator lock 1012 permits the primary actuator 1010 to slide along the axis 1001, as further described below. The secondary actuator 1020 includes an actuator knob 1022 that is engageable to rotate the secondary actuator 1020 through the curve 1003 around the axis 1001, as also further described below. As also further described below, in various embodiments, actuator interlocks restrict movement of the secondary actuator 1020 until the primary actuator 1010 is moved to extend the primary electrode 207 (not shown in FIG. 10), and restrict movement of the primary actuator 1010 once the secondary actuator 1020 is moved to extend the secondary electrode 211.

Figure 11:
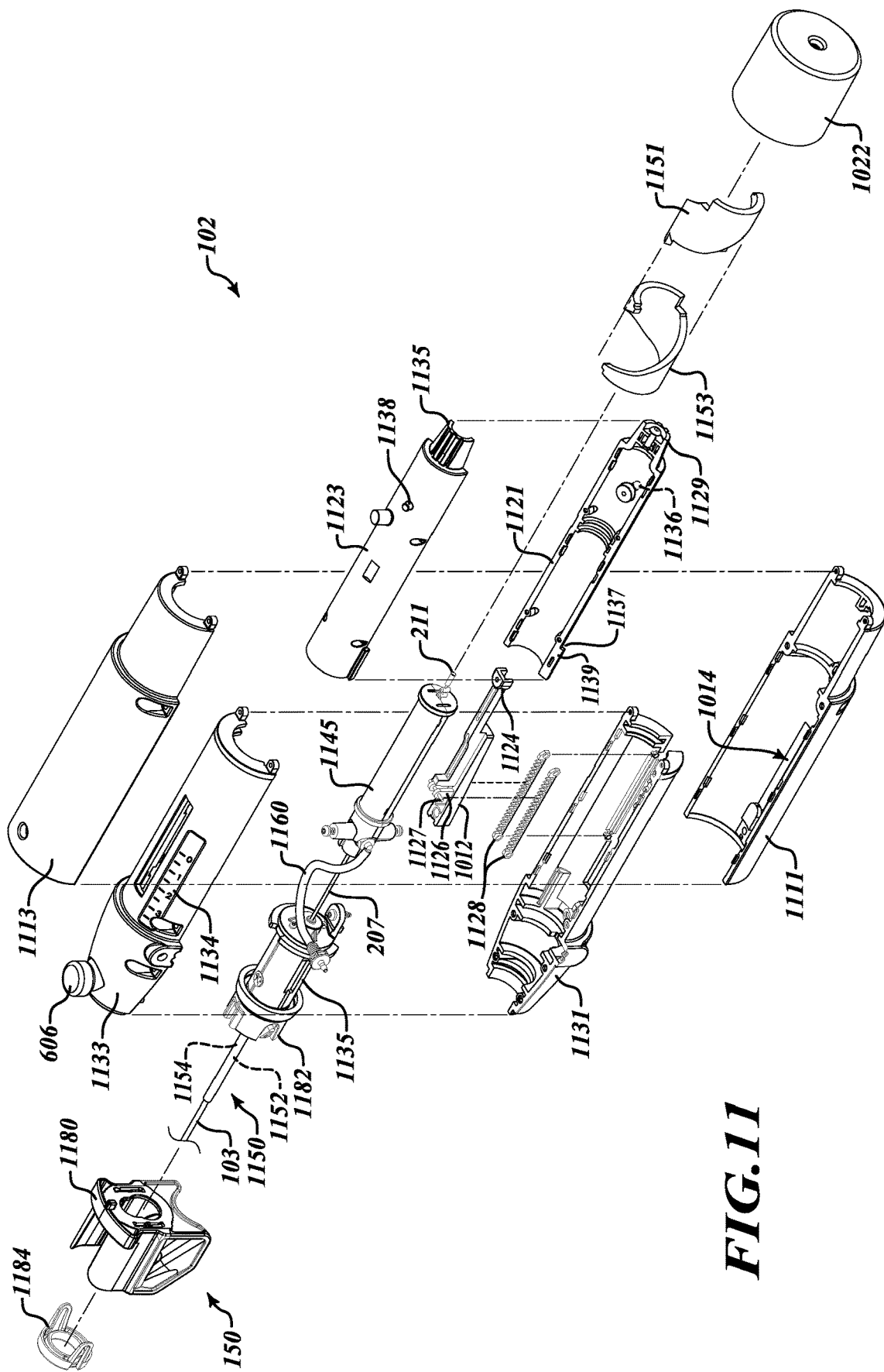
FIG. 11 is an exploded view of the user interface of FIG. 10.

Referring to FIG. 11, various components of the user interface 102, including portions of the housing 610, the primary actuator 1010, and the secondary actuator 1020 illustrate the interrelationship of the components in various embodiments. The housing 610 (FIG. 10) includes a first housing section 1131 and a second housing section 1133. The housing sections 1131 and 1133 have hollow interiors to receive and permit movements of other components arranged therein. A first housing section 1131 internally supports a locking rack 1128 that engages the actuator lock 1012. More specifically, the locking rack 1128 includes recesses having openings facing inwardly into the housing 610 to permit selective engagement with the actuator lock 1012. The second housing section 1133 also may include a depth scale 1134 that may be used to visually gauge a position of the primary electrode 207 based on a position of the primary actuator 1010 relative to the housing 610. A second housing section 1133 threadably supports the sheath lock 606, which is part of the sheath actuator 604, as previously described with reference to FIGS. 6A-9. The housing sections 1131 and 1133 are matable sections, joinable by adhesives or fasteners, such as screws (not shown in FIG. 11).

In various embodiments, primary actuator sections 1111 and 1113 are slidably received around the housing section 1131 and 1133. The primary actuator sections 1111 and 1113 are have generally hollow interiors to slidably receive the housing sections 1131 and 1133 therebetween. A first primary actuator section 1111 defines the actuator opening 1014 that receives the actuator lock 1012. The actuator lock 1012 has a base 1124 that is fixably securable to the first primary actuator section 1111 and around which the actuator lock 1012 partially rotates into an opening or recess (not shown in FIG. 11) in the housing 610 when the actuator lock 1012 is depressed. At an end opposite the base 1124, the actuator lock 1012 also supports a pin support 1126 that holds a pin 1127 that engages the locking rack 1128 of the first housing section 1131 when the actuator lock 1012 is not depressed.

In various embodiments, the actuator lock 1012 is biased into a locking position where the pin support 1126 causes the pin 1127 to engage the locking rack 1128 when the actuator lock 1012 is released. The actuator lock 1012 may be biased by rigidity of the actuator lock 1012 causing the actuator lock 1012 to resume its undeformed position when the actuator lock 1012 is released. Alternatively, the actuator lock 1012 may be spring loaded by a spring actuator (not shown) positioned between the actuator lock 1012 and the housing 610. The primary actuator sections 1111 and 1113 are joinable by adhesives or fasteners, such as screws (not shown in FIG. 11).

Another portion of the primary actuator 1010 is a secondary actuator guide, comprised of guide sections 1151 and 1153 couplable to the primary actuator sections 1111 and 1113. As described in more detail with reference to FIGS. 22 and 23, the guide sections 1151 and 1153 are joinable at their ends to form an annular tube and, between their respective edges, define a helical channel that receive guide members 1136 and 1138 extending outwardly from secondary actuator sections 1121 and 1123. The engagement of the guide members 1136 and 1138 with the helical channel defined by edges of the guide sections 1151 and 1153, with reference to FIG. 10, cause the secondary actuator 1020 to advance along the axis 1001 when the secondary actuator 1020 is rotated through a curve 1003 around the axis 1001.

In various embodiments, secondary actuator sections 1121 and 1123 are rotatably mounted between the housing sections 1131 and 1133. The secondary actuator sections 1121 and 1123 are generally hollow to receive therebetween other components of the user interface 102. As previously described, each of the secondary actuator sections 1121 and 1123 outwardly support the guide members 1136 and 1138 that engage the helical channel defined by edges of the guide sections 1151 and 1153. Ends 1129 and 1139 of the respective secondary actuator sections 1121 and 1123 are shaped to engage the actuator knob 1022 used to rotate the secondary actuator 1020, as will be further described below with reference to FIGS. 16A and 17A. The secondary actuator sections 1121 and 1123 are joinable by adhesives or fasteners, such as screws (not shown in FIG. 11).

In various embodiments, the primary actuator 1010 and the secondary actuator 1020 include actuator interlocks to control relative movement of the actuators 1010 and 1020. In various embodiments, a first secondary actuator half 1121 may support a recess 1137 and a locking member 1139 to control relative movements of the primary actuator 1010 and the secondary actuator 1020. The recess 1137 may be configured to receive the pin support 1126 extending from the actuator lock 1012 to enable the actuator lock 1012 to be depressed to advance the primary actuator 1010. However, after the primary actuator 1010 is moved, the actuator lock 1012 is released, and the secondary actuator 1020 is rotated, the rotation of the secondary actuator 1020 results in the recess 1137 being displaced from under the pin support 1126. As a result of the displacement, the actuator lock 1012 is no longer depressible because a body of the secondary actuator 1020 blocks the pin support 1126, thereby preventing depressing of the actuator lock 1012. However, after the secondary actuator 1020 is returned to its starting position, the recess 1137 again rotates beneath the pin support 1126, allowing depressing of the actuator lock 1012 to permit movement of the primary actuator 1010.

Similarly, to prevent rotation of the secondary actuator 1020 before the primary actuator 1010 is moved to deploy the primary electrode 207, the locking member 1139 may engage a notch (not shown) in the housing 610. After the actuator lock 1012 is depressed and the primary actuator 1010 is moved relative to the housing 610 to deploy the primary electrode 207, the locking member 1139 clears the housing 610. It should be noted that the recess 1137 will continue to receive the pin support 1126 as long as the actuator lock 1012 is depressed, continuing to prevent rotation of the secondary actuator 1020. Once the actuator lock 1012 is disengaged, the secondary actuator 1020 is rotatable to deploy the secondary electrode 211 and to block the actuator lock 1012 from being engaged to permit movement of the primary actuator 1010. Thus, in sum, the actuator interlocks ensure that the primary actuator 1010 be moved to deploy the primary electrode 207 before the secondary actuator 1020 may be rotated. Then, once the primary actuator 1010 has been moved to deploy the primary electrode 207 and the secondary actuator 1020 is rotated from its starting position, the actuator interlocks prevent the primary actuator 1010 and the primary electrode 207 from being moved until the secondary actuator 1020 is moved to retract the secondary electrode 211 to its original position.

The user interface 102 also includes a sheath mount 1135 that is receivable between the housing sections 1131 and 1133 to mechanically engage the housing 610 with the sheath 103. As a result, as described with reference to FIGS. 6A-9, movement of the housing 610 extends or retracts the sheath 103. The user interface also includes electrode sliders coupled with the respective electrodes 207 and 211. A primary electrode slider 1145 is mechanically engageable by the primary actuator sections 1113 and 1133 so that sliding the primary actuator 1010 advances or retracts the primary electrode slider 1145 to advance or retract the primary electrode 207, respectively. A secondary electrode slider (not shown in FIG. 11) mechanically engageable by the secondary actuator sections 1121 and 1123 is slidably received within the primary electrode slider 1145. Because the secondary actuator sections 1121 and 1123 are rotatably moved, as further described below, the secondary electrode slider is also rotatably received between the secondary actuator sections 1121 and 1123.

A flexible wiring harness 1150 is configured to receive one or more conductors of the electrical conductor 130 (FIG. 1) at a port on the housing 610 (not shown in FIG. 11), and to electrically connect with flexible leads 1152 and 1154, each of which connects with one of the electrodes 207 and 211. The flexible leads 1152 and 1154 are configured to remain electrically connected with the electrodes 207 and 211 as proximal ends of the electrodes 207 and 211 are moved within the user interface 102.

Additionally, a flexible fluid coupling 1160 extends from a fluid port (not shown in FIG. 11) on the housing 610 to an interior of the primary electrode slider 1145 to convey fluid into a lumen defined within the primary electrode 207. The fluid port receives the tube 132 from the infusion pump 116 (FIG. 1) at the housing 610 to receive a flow of conductive fluid. The flexible fluid coupling 1160 may be coiled within the housing 610 to permit extension and contraction of the fluid coupling 1160 with the movement of the primary electrode slider 1145 relative to the housing 610.

As further described below with reference to FIGS. 27 and 28, the coupler 150 includes a slidable locking body 1180 that is slidably received between a slidable mount 1182 and a retaining ring 1184. The slidable mount 1182 is coupled with the housing 610. As further described below, once the housing 610 is positioned to engage the electrosurgical device 118 (not shown in FIG. 11), the locking body 1180 is slid into place to secure the connection, as further described with reference to FIGS. 27 and 28.

Referring to FIGS. 12A-21B, operation of the user interface 102 and corresponding movements of the sheath 103, the primary electrode 207, and the secondary electrode 211 are described.

Figure 12A:
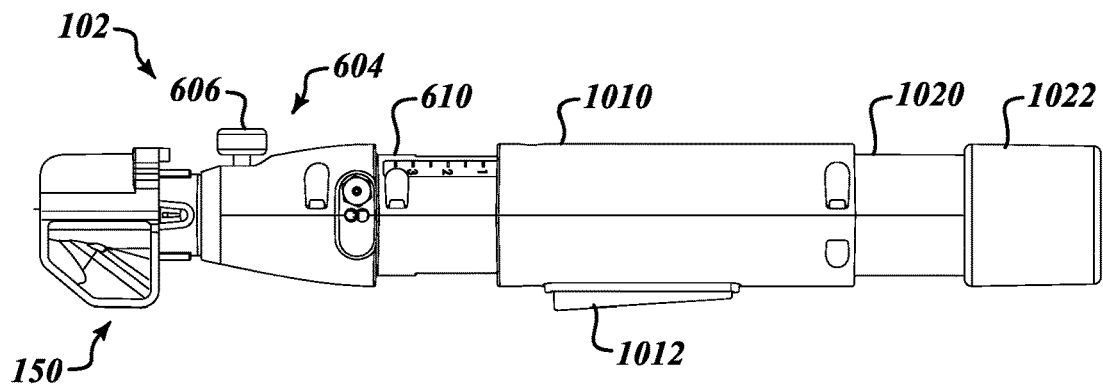
Figure 12B:
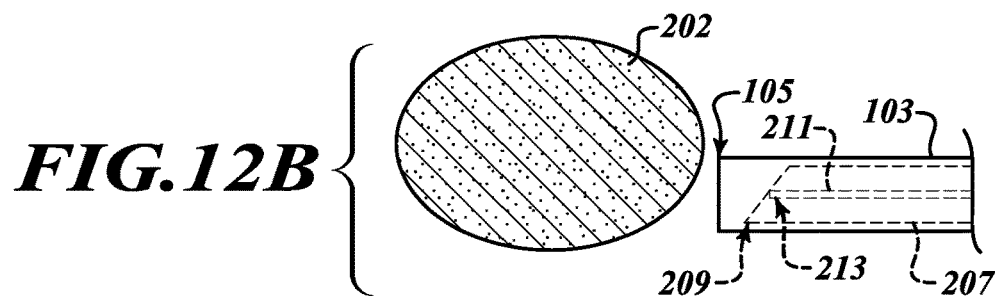

Referring to FIGS. 12A and 12B, the distal end 105 of the sheath 103 is positioned adjacent to the target region 202. As previously described with reference to FIGS. 6A-7B, in various embodiments, the sheath actuator 604 enables the sheath 103 to be positioned by releasing the sheath lock 606 and moving the housing 610. For example, referring again to FIGS. 6A-7B, a position of the sheath 103 is controlled by sliding the slidable sleeve 612 within the collar 614, then securing the sheath 103 at the desired location by reengaging the sheath lock 606. When the distal end 105 of the sheath 103 is deployed adjacent to the target region 202, a distal end 209 of the primary electrode 207 lies just within the distal end 105 of the sheath 103. At the same time, the distal end 213 of the secondary electrode 211 lies just within the distal end 209 of the primary electrode 207. With the distal end 105 of the sheath 103 positioned adjacent the target region 202, the user interface 102 may be used to move the electrodes 207 and 211 to desired positions.

Figure 13A:
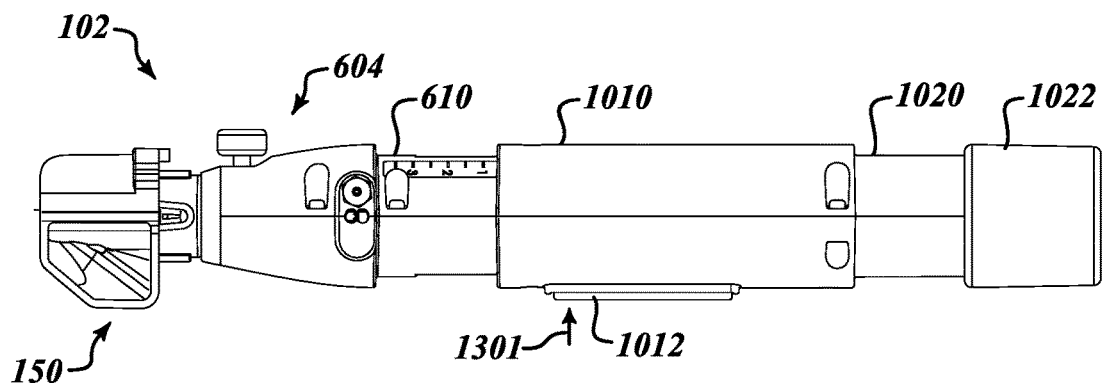
Figure 13B:
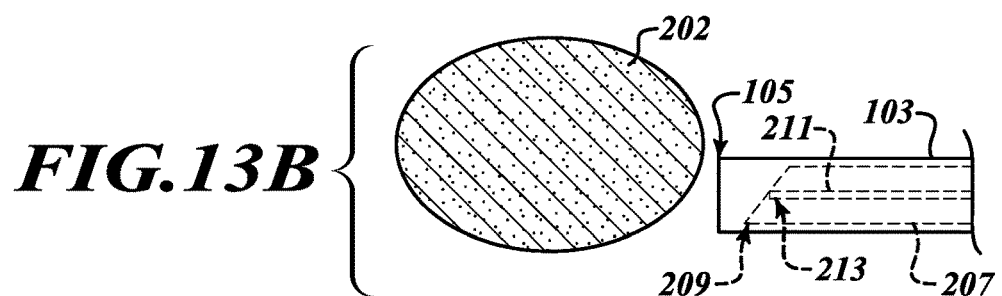

Referring to FIGS. 13A and 13B, according to various embodiments, positioning the electrodes 207 and 211 begins with depressing the actuator lock 1012 to enable movement of the primary actuator 1010. Depressing the actuator lock 1012 to move the actuator release 1012 in a direction 1301 disengages the primary actuator 1010 from the housing 610. Specifically, depressing the actuator lock 1012, which is hingeably or rotatably coupled with the primary actuator 1010 at the base 1124, causes the pin support 1126 to move the pin 1127 from inward-facing recesses of the locking rack 1128 on the housing 610. With the pin 1127 removed from the locking rack 1128, the primary actuator 1010 is movable relative to the housing 610 to move the primary electrode 207, as described with reference to FIGS. 14A and 14B.

As previously described, the secondary actuator 1020 is rotatably engaged with the primary actuator 1020. Accordingly, the secondary actuator 1020 remains engaged with the primary actuator 1010 even when the actuator lock 1012 is released to release the primary actuator 1010 from the housing 610. Therefore, depressing the actuator lock 1012 frees the primary actuator 1010 and the secondary actuator 1020 to move collectively, thus enabling the primary electrode 207 and the secondary electrode 211 to be moved collectively.

Figure 14A:
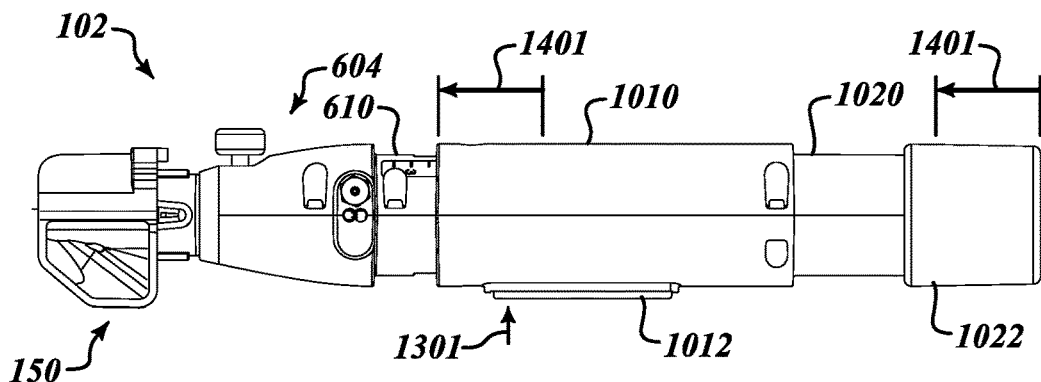
Figure 14B:
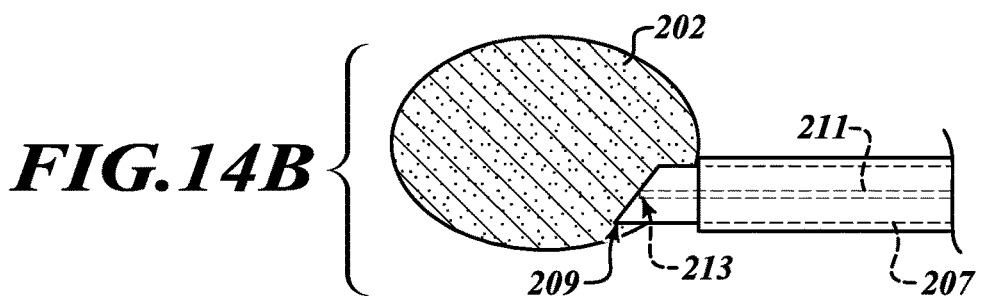

Referring to FIGS. 14A and 14B, while a user continues to depress the actuator lock 1012 in the direction 1301, the primary actuator 1010 is moved in a direction 1401. Because the secondary actuator 1020 remains (rotatably) engaged with the primary actuator 1010 as previously described, the primary actuator 1010 and the secondary actuator move collectively the same distance in the direction 1401, as represented in FIG. 14A.

As a result of the collective movement of the primary actuator 1010 and the secondary actuator 1020, the primary electrode 207 and the secondary electrode 211 move collectively as well. Thus, as depicted in FIG. 14B, the distal end 209 of the primary electrode 207 and the distal end 213 of the secondary electrode 211 move collectively beyond the distal end 105 of the sheath 103 into the target region 202. Thus, by virtue of the engagement of the secondary actuator 1020 with the primary actuator 1010, depressing the actuator lock 1012 and moving the primary actuator 1010 moves both electrodes 207 and 211 collectively.

As previously described with reference to FIG. 11, with the actuator lock 1012 depressed, in various embodiments, the pin support 1026 on the actuator release 1012 engages the secondary actuator 1020, preventing the secondary actuator 1020 from being rotated until the actuator release 1012 is disengaged. As also previously described, the secondary actuator 1020 may include the locking member 1139 that abuts the housing 610. This arrangement prevents the secondary actuator 1020 from being rotated before the actuator lock 1012 is depressed and the primary actuator 1010 and the secondary actuator 1020 are advanced.

Figure 15A:
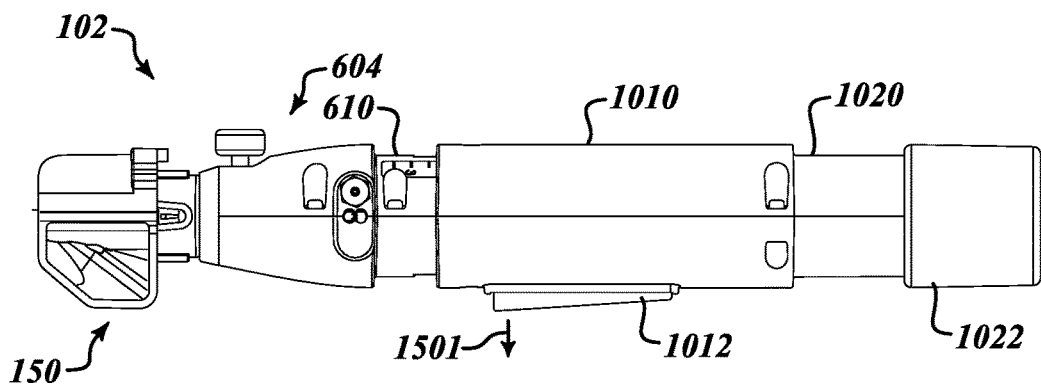
Figure 15B:
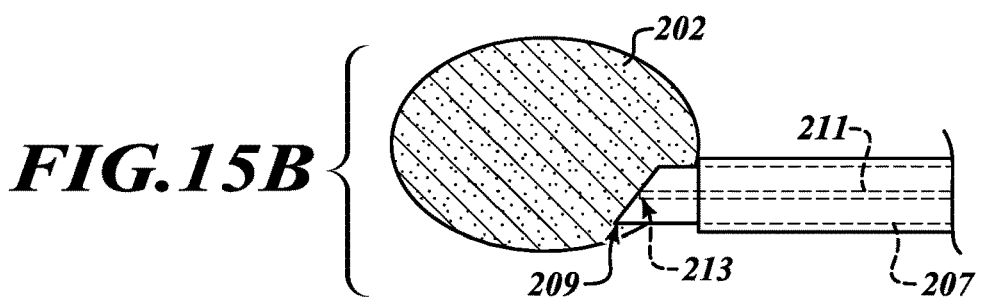

Referring to FIGS. 15A and 15B, once the distal ends 209 and 213 of the primary electrode 207 and the secondary electrode 211, respectively, have been advanced into the target region 202, the actuator lock 1012 is released. Because the actuator lock 1012 is biased by its rigidity or by a spring, as described with reference to FIG. 11, releasing the actuator lock 1012 results in the actuator lock 1012 moving in a direction 1501. The movement of the actuator lock 1012 causes the primary actuator 1010—and the rotatably engaged secondary actuator 1020—to again be engaged with the housing 610, holding the electrodes 207 and 211 in place. As described with reference to FIG. 11, when the actuator lock 1012 is released, a pin 1127 mounted in the pin support 1026 moves into recesses in the locking rack 1128 mounted on the housing 610. Thus, the engagement of the pin 1127 with the locking rack 1128 prevents further movement of the primary actuator 1010 until the actuator lock 1012 is further engaged by a user. Accordingly, with the user releasing the actuator lock 1012, the distal ends 209 and 213 of the primary electrode 207 and the secondary electrode 211 are secured in the locations to which they were moved as described with reference to FIGS. 14A and 14B.

Figure 16A:
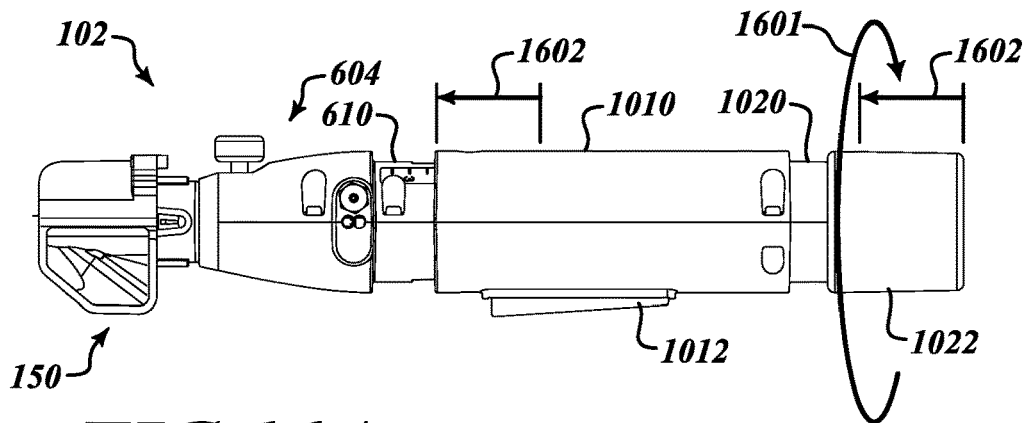
Figure 16B:
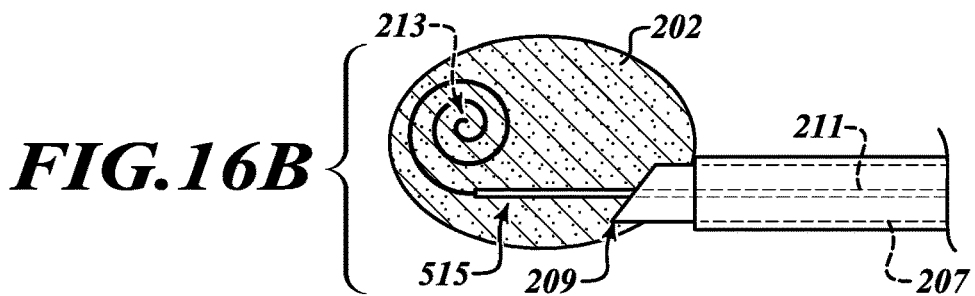

Referring to FIGS. 16A and 16B, with the primary actuator 1010 held in place by the user's release of the actuator lock 1012, the secondary actuator 1020 is rotated to move the secondary electrode 211 independently of the primary electrode 207. As shown in FIG. 16A, the secondary actuator 1020 is moved by a user rotating the actuator knob 1022 in a direction 1601. As previously described with reference to FIG. 11, the secondary actuator 1020 supports guide members 1136 and 1138 that are received within the helical channel defined between edges of the guide sections 1151 and 1153. With the secondary actuator 1020 engaged with the helical channel defined by the guide sections 1151 and 1153, rotation of the actuator knob 1022 results in helical movement of the secondary actuator 1020. The rotation of the secondary actuator 1020 thus causes the secondary actuator 1020 to advance in a direction 1602 relative to the primary actuator 1010 and the housing 610.

Referring to FIG. 16B, movement of the secondary actuator 1020 results in the distal end 213 of the secondary electrode 211 extending beyond the distal end 207 of the primary electrode 209. As previously described with reference to FIG. 5, the distal end 213 of the secondary electrode 211 may be preformed into a coiled shape, thereby resulting in the secondary electrode 211 forming a coiled shape once the secondary electrode 211 is no longer constrained within the lumen of the primary electrode 207. In various embodiments, the coiled shape at the distal end 213 of the secondary electrode 211 augers into the tissue of the target region 202, which secures the secondary electrode 211—and the primary electrode 207 through which it extends—in position at the target region 202. The insulated section 515 of the secondary electrode 211 electrically insulates the secondary electrode 211 from the primary electrode 207 except as between their respective distal ends 213 and 209. With the distal ends 213 and 209 of the electrodes 211 and 207 deployed, a supply of conductive fluid and/or electrical current may be applied to the target region 202 as previously described to effect treatment.

The actuator interlocks presented by the configuration of the actuators 1010 and 1020 prevent the user from moving the primary actuator 1010 once the secondary actuator 1020 is rotated from its original position. As previously described with reference to FIG. 11, rotating the secondary actuator 1020 blocks the pin support 1126 of the actuator lock 1012, thereby preventing a user from depressing the actuator lock 1012 to release the primary actuator 1010 from its engagement with the housing 610 via the pin 1127 and the locking rack 1128. Thus, the distal end 209 of the primary electrode 207 remains in place as inserted into the target region 202 while the secondary actuator 1020 is moved to extend the distal end 213 of the secondary electrode 211 into the target region 202.

Deployment of the sheath 103 and the electrodes 207 and 211 to permit the application of treatment is described with reference to FIGS. 6A-7B and 12A-16B. Conversely, to withdraw and move the electrodes 207 and 211 from the target region 202, manipulations and the sequence of manipulations of the user interface 102 is reversed, as described with reference to FIGS. 17A-21B.

Figure 17A:
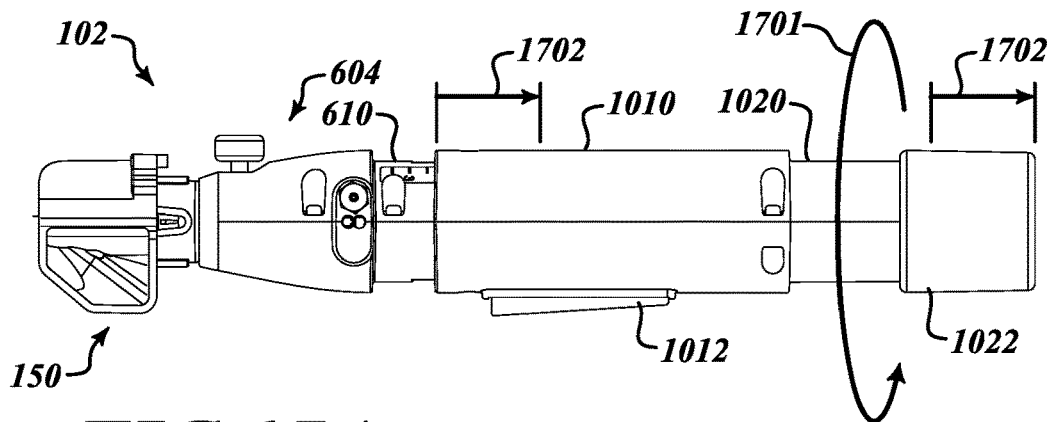
Figure 17B:
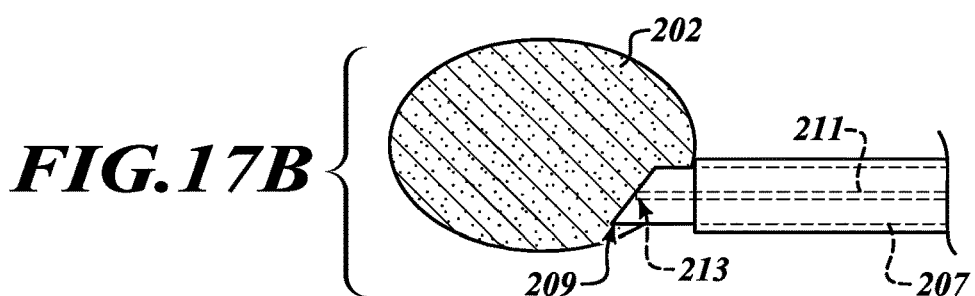

Referring to FIGS. 17A and 17B, the distal end 213 of the secondary electrode 211 is retracted into the primary electrode 207 by a user rotating the actuator knob 1022 in a direction 1701. The direction 1701 in which the actuator knob 1022 is rotated to retract the distal end 213 of the secondary electrode 211 from the target region 202 is opposite to the direction 1601 in which the actuator knob 1022 was rotated to extend the distal end 213 of the secondary electrode 211. Rotation of the actuator knob 1022 results in an opposite, helical movement of the secondary actuator 1020, resulting the secondary actuator 1020 translating in a direction 1702 relative to the primary actuator 1010 and the housing 610. The movement of the secondary actuator 1020 withdraws the secondary electrode 211 until the distal end 213 of the secondary electrode 211 again is received within the distal end 209 of the primary electrode 207. With the secondary actuator 1020 moved to its original position relative to the primary actuator 1010, the actuator lock 1012 now may be released, as described with reference to FIG. 18A. It will be appreciated that retraction of the secondary electrode 211 is accomplished by rotating the secondary actuator 1020 while the primary actuator 1010 remains stationary.

Figure 18A:
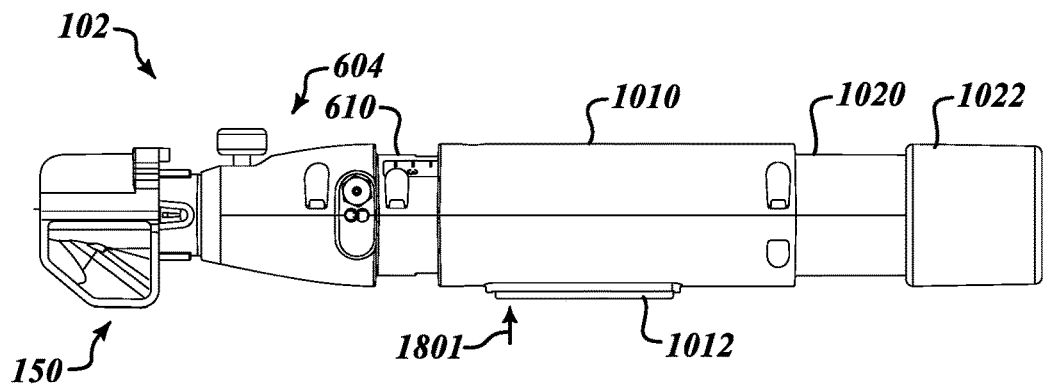
Figure 18B:
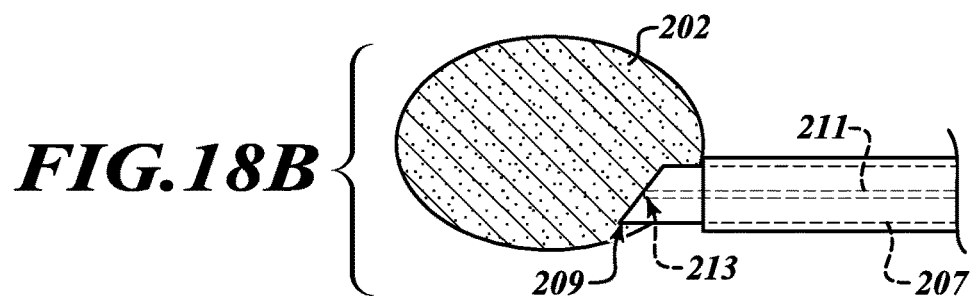

Referring to FIGS. 18A and 18B, to prepare for retraction of the primary electrode 207 from the target region 202, the actuator lock 1012 is depressed by a user in a direction 1801. Depressing the actuator lock 1012 does not result in any movement of the distal ends 209 and 213 of the electrodes 207 and 211, respectively, just as engagement of the actuator lock 1012 did not result in movement of the electrodes 207 and 211 when the actuator lock 1012 was depressed and released as previously described with reference to FIGS. 13A and 13B and FIGS. 15A and 15B, respectively.

Figure 19A:
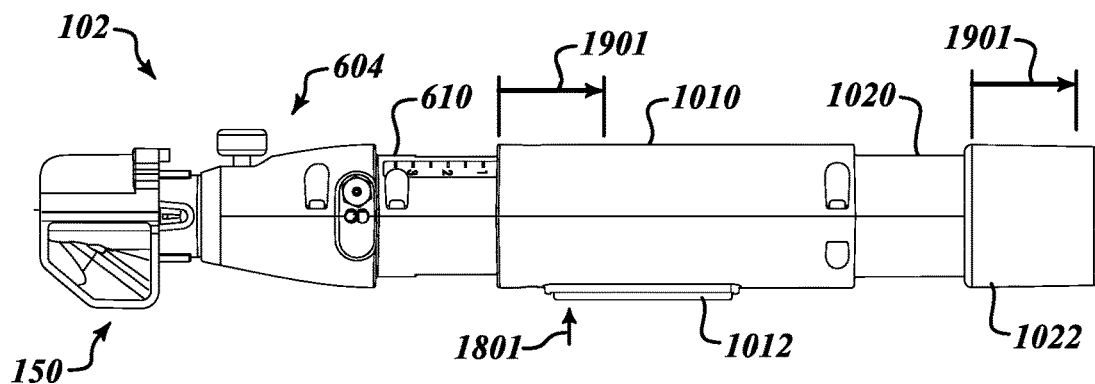
Figure 19B:
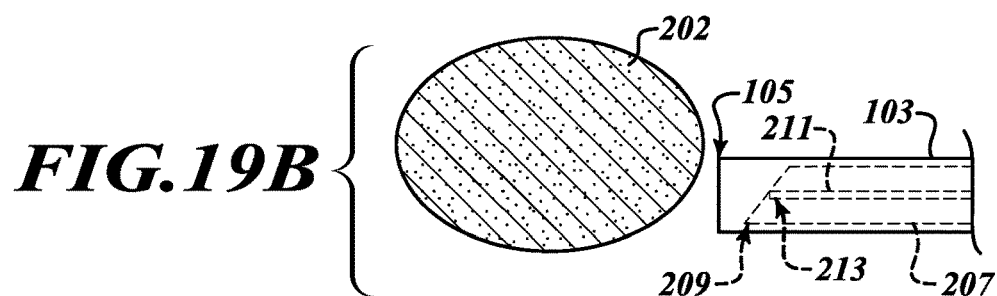

Referring to FIGS. 19A and 19B, with the actuator lock 1012 depressed, the primary actuator 1010 is moved in a direction 1901 to withdraw the distal end 209 of the primary electrode 207 from the target region 202. As previously described with reference to FIGS. 14A and 14B, because the secondary actuator 1020 remains rotationally engaged with the primary actuator 1010, the secondary actuator 1020 also moves a same distance and in the same direction 1901 as the primary actuator 1010. As a result, the distal ends 209 and 213 of the electrodes 207 and 211 are moved collectively and withdrawn from the target region 202. After the primary actuator 1010 is fully retracted in the direction 1901, the distal end 209 of the primary electrode 207 is received within the distal end 105 of the sheath. Further, because the secondary actuator 1020—and, thus, the secondary electrode 211—moves in concert with the primary actuator 1010, the distal end 213 of the secondary electrode 211 remains within the distal end 209 of the primary electrode 207 as the distal end 209 of the primary electrode 207 is withdrawn within the distal end 105 of the sheath 103.

Figure 20A:
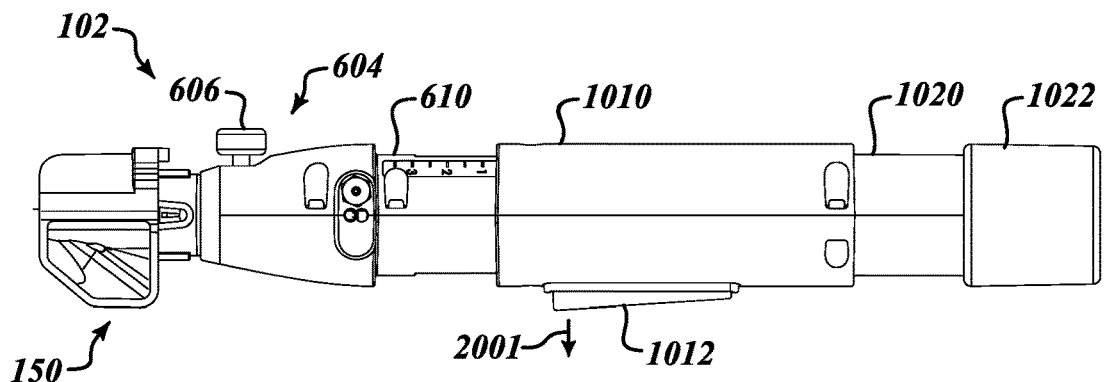
Figure 20B:
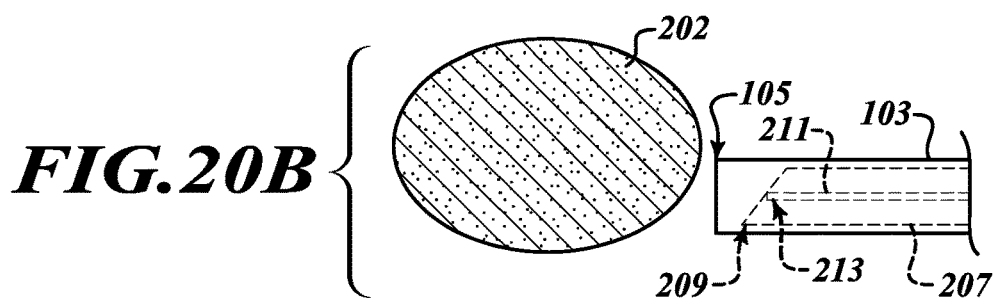

Referring to FIGS. 20A and 20B, once the distal ends 209 and 213 of the electrodes 207 and 211, respectively, are withdrawn within the distal end 105 of the sheath 103, the actuator lock 1012 is released. Upon release of the actuator lock 1012, the actuator lock 1012 moves in a direction 2001. As a result, the pin 1127 held by the pin support 1126 reengages the locking rack 1128 to hold the primary actuator 1010 in place. Further, as previously described, the actuator interlocks that prevent the secondary actuator 1020 from being rotated, such as by the locking member 1139 extending from the secondary actuator 1020 engaging the housing 610, prevents rotation of the secondary actuator 1020 while the actuators 1010 and 1020 have resumed a starting position as described with reference to FIGS. 12A and 12B.

Figure 21A:
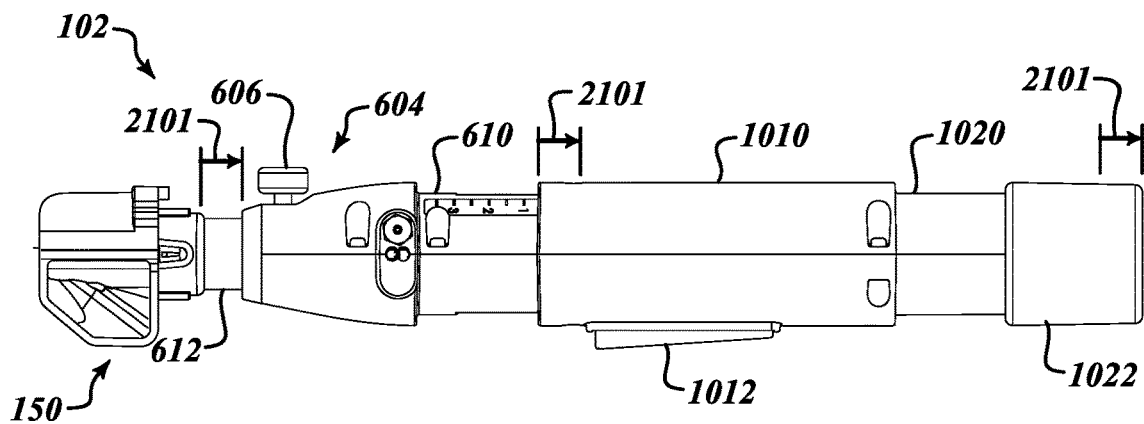
Figure 21B:
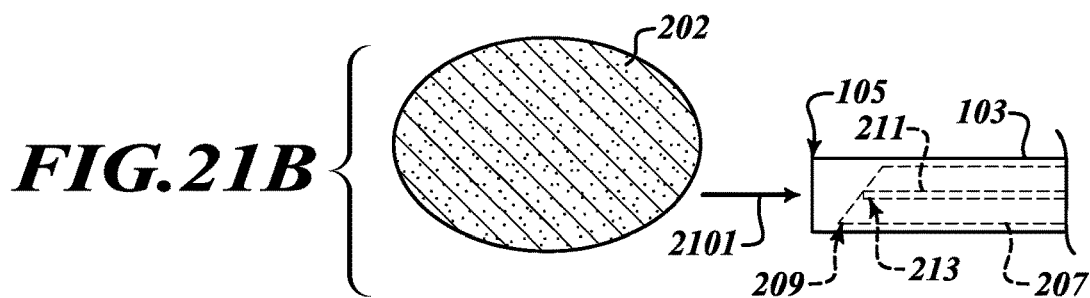

Referring to FIGS. 21A and 21B, with distal ends 209 and 211 of the electrodes 207 and 211, respectively, withdrawn within the distal end 105 of the sheath 103, the sheath 103 itself may be withdrawn. In an operation opposite that depicted in FIGS. 7A and 7B, the sheath lock 606 is released and the housing 610 is moved along the slidable sleeve 612 in a direction 2101 away from the coupling 150. Because the primary actuator 1010 is locked to the housing by the actuator lock 1012, and the secondary actuator 1020 is rotatably secured to the primary actuator 1010, the primary actuator 1010 and the secondary actuator 1020 move in concert with the housing 610 in the direction 2101. The sheath 103 and the insertion tube 119 (FIG. 1) of the electrosurgical device 118 may then be withdrawn from the body. Alternatively, without withdrawing the sheath as described with reference to FIGS. 21A and 21B, once the electrodes 207 and 211 are withdrawn into the sheath as described with reference to FIGS. 19A-20B, the sheath 103 may be withdrawn from the body without first withdrawing the sheath 103 by engaging the sheath lock 606.

As previously described with reference to FIGS. 11, 16A, and 17A, the secondary actuator 1020 supports guide members 1136 and 1138 that engage a helical channel defined by edges of guide sections 1151 and 1153. Referring to FIG. 22, the guide sections 1151 and 1153 are mated together into a guide sleeve 2202 as they are when joined with the primary actuator 1010. The guide sections 1151 and 1153 may be joined at ends 2215 and 2217. Specifically, as shown in FIG. 23, sockets 2330 may be supported by the guide sections 1151 and 1153 enabling the guide sections to be connected by screws, dowels, or other fasteners.

Between the ends 2215 and 2217 of the guide sleeve 2202, edges 2211 and 2213 of the guide sections 1151 and 1153 define a helical channel 2201. The helical channel 2201 guides the movement of the support members 1136 and 1138 to cause the secondary actuator 1020 to translate in response to rotation of the secondary actuator as described with reference to FIGS. 16A and 17A.

In various embodiments, the generally helical channel 2201 has a varied pitch between the ends 2215 and 2217 of the guide sleeve 2202. In various embodiments, the pitch may vary from a rearward end 2215, where the secondary actuator 1020 begins its helical movement to extend the secondary electrode 207, toward a forward end 2217. More specifically, in various embodiments, the pitch of the helical channel is varied to reduce a distance of travel of the secondary actuator 1020 along the axis 1001 of the user interface 102 (not shown in FIG. 22) per unit of rotation of the secondary actuator 1020 from the rearward end 2215 toward the forward end 2217.

In various embodiments, the pitch is varied in this manner to reduce the rotational force to be applied by a user in turning the actuator knob 1022 to motivate the secondary actuator 1020. For example, considering FIGS. 5 and 16B, as the distal end 213 of the secondary electrode 211 is advanced into the target region 202, the distal end 213 of the secondary electrode 211 may encounter increased resistance. Part of this resistance results from the distal end 213 of the secondary electrode 211 frictionally engaging a mass in the target region along an increasing length of the secondary electrode 211 as a longer section of the secondary electrode 211 is extended further beyond the distal end 209 of the primary electrode 207. Part of this resistance may also result from the curvature of the of the coil at the distal end 213 of the secondary electrode 211 encountering an increasing degree of resistance in augering into the mass at the target region 202. Correspondingly, greater force may be involved at the start of withdrawal of the secondary electrode 211 in frictionally engaging a greater mass of tissue than when the secondary electrode 211 is closer to being fully retracted into the distal end 209 of the primary electrode 207. Further, when a portion of the secondary electrode 211 near the distal end 213 is formed into a coiled shape using a memory alloy, withdrawing the secondary electrode 207 may involve application of additional force in seeking to draw the secondary electrode into a deformed, straightened shape that the secondary electrode 211 assumes when confined within the primary electrode 207.

As a result, in deploying the secondary electrode 211, more force may be involved in extending the secondary electrode 211 as the secondary electrode 211 extends further beyond the distal end 209 of the primary electrode 207 into the target region 202. As a result, a greater degree of rotational force may be involved in rotating the actuator knob 1022 of the secondary actuator 1020 as the secondary actuator 1020 moves toward the forward end 2217 of the guide sleeve 2202. Correspondingly, more force may be involved the initial portion of withdrawing the secondary electrode 211 than when the secondary electrode 211 has been or nearly has been fully retracted into the primary electrode 207. Therefore, a greater degree of rotational force may be involved in rotating the actuator knob 1022 of the secondary actuator 1020 as the secondary actuator 1020 first moves away from the forward end 2217 of the guide sleeve 2202.

According to various embodiments, the pitch of the helical channel 2201 may be varied between the trailing end 2215 and the forward end 2217 of the guide sleeve 2202. Specifically, the pitch of the helical channel 2201 may be varied to reduce a distance of travel of the second actuator 1020 along the axis 1001 per unit of rotation through the curve 1003 around the axis 1001 toward the forward end 2217 of the guide sleeve 2202 facing a forward end of the user interface 2202. By reducing the distance of travel of the second actuator 1020 toward the forward end of the guide sleeve 2202, the increased force along the axis 1001 is effectively spread over a greater degree of rotation of the second actuator 1020. Thus, while lateral resistance to moving the secondary electrode 211 along the axis 1001 may increase at a forward end 2217 of the guide sleeve 2202, the force involved in rotating the actuator knob 1022 to rotate the secondary actuator 1020 does not increase as much.

Referring to FIG. 23, because the pitch of the helical channel 2201 is defined by the edges 2211 and 2213 of the guide sections 1151 and 1153, respectively, a pitch of the edges 2211 and 2213 is varied to define a helical channel 2201 of a desired shape. For example, considering the first guide section 1153, at a first point 2301 toward a rearward end 2345 of the first guide section 1153, a pitch angle α of the edge 2213 (as measured tangentially to the edge 2213 relative to the axis 1001) is greater than a pitch angle β at a second point 2302 moving toward the forward end 2347 of the first guide section 1153. Similarly, the pitch angle β at the second point 2302 is greater than a pitch angle γ at a third point 2303 moving further toward the forward end 2347 of the guide section 1153. A corresponding arrangement is repeated with the second guide section 1151, with a pitch angle along the edge 2211 becoming less moving from a rearward end 2341 of the second guide section 1151 toward the forward end 2343. As a result, despite increased resistance along the axis 1001, rotational resistance applied to the secondary actuator 1020 is reduced by the decreasing pitch of the helical channel 2201 (FIG. 22) defined by the decreasing pitch of the edges 2211 and 2213 of the respective guide sections 1151 and 1153.

In addition to varying the pitch of the helical channel 2201 to facilitate deployment and withdrawal of the secondary electrode 207, a cross-section of the wire used as the secondary electrode 207 also may ease the deployment and withdrawal of the secondary electrode 207. Referring to FIGS. 24-26, the secondary electrode 207 may include a wire having portions 2410 and 2420 of different thicknesses along its length.

Referring to FIG. 24, a first portion 2410 of the secondary electrode 207 may have a circular cross-section with a first thickness 2412. A second portion 2420 leading to the distal end 213 of the secondary electrode 211 may have a flat or rectangular cross-section having a second thickness 2422 that is less than the first thickness 2412. In an illustrative embodiment, the first thickness 2412 of the circular cross-section of the first portion 2410 may be 0.015 inches, and the second thickness 2422 of the second portion may be 0.009 inches. In such a configuration, a theoretical moment of inertia for the first portion 2410 is more than twice that of a theoretical moment of inertia for the second portion 2420. The greater theoretical moment of inertia of the first portion 2410 thus should improve the force transmission of the first portion 2410 in advancing the secondary electrode 207 without impeding the capacity of the second portion 2420 to assume its coiled configuration upon deployment. The first thickness 24212 is aligned with an axis 2430 that defines a plane in which the second portion 2402 will coil, as depicted in FIG. 25.

Referring to FIG. 26, the secondary electrode 211 is in an uncoiled configuration. The second portion 2420 may have a second width 2624 that is wider than the second thickness 2422 of the second portion 2420 and wider than the first thickness 2412 of the first portion 2410. In a non-limiting example, the first thickness 2412 may be 0.015 inches, the second thickness may be 0.009 inches, and the second width may be 0.020 inches.

A secondary electrode 211 with the first portion 2410 having a circular cross-section provides good column strength and force transmission for motivating the secondary electrode 211 along its length. The column strength and force transmission are helpful in driving the secondary electrode 211 through the lumen within the primary electrode 207 and in extending the secondary electrode 211 into a tissue at a target region, as depicted in FIG. 5. By contrast, with the second portion 2420 having a reduced thickness in the plane in which the second portion 2420 of the secondary electrode 211 is to coil makes it easier for the secondary portion to assume its coiled shape. Using the exemplary dimensions, the moment of inertia of the second portion 2420 is less than half of that of the first portion 2410, reducing the force required to coil and uncoil the second portion 2410. Having a second width 2624 that is larger than the second thickness 2422 and larger than the first thickness 2412 improves the column strength and force transmission of the second portion 2420 to keep the second portion 2420 from buckling, while still having a thinner second thickness 2422 that facilitates the coiling of the second portion 2420.

Referring to FIG. 27, the coupler used to secure the user interface 102 with the electrosurgical device 118 includes a slidable mounting mechanism 2710 and a locking body 2720. In various embodiments, the slidable mounting mechanism 2710 is secured to the slidable sleeve 612 extending from the housing of the user interface (not shown in FIG. 27) and fits around the slidable sleeve 612. The slidable sleeve 612 has an internal width 2791 that is sized to receive a flange 2754 at an end of a device interface 2752. The flange 2754 has an outer width 2793 that is less than the internal width 2791 of the slidable sleeve 612 so that the flange 2754 is receivable within an end of the slidable sleeve 612. The device interface 2752 has an outer width 2795 that is less than the outer width 2793 of the flange 2754 that it abuts. The outer width 2795 of the device interface 2795 and the outer width 2793 of the flange 2754 are considered in the configuration of the locking body 2720, as further described below with reference to FIG. 28.

The slidable mounting mechanism 2710 includes a base portion 2712 that is fixed, fixable, or connected to the slidable sleeve 612 (the slidable mounting mechanism 2710 is shown in FIG. 27 prior to being fixably connected to the slidable sleeve 612). The slidable mounting mechanism 2710 also includes one or more projections 2714 that are configured to receive retaining clips 2734 extending from a retaining ring 2730 to secure the lock plate 2720 to the slidable mounting mechanism 2710, as further described below.

The slidable mounting mechanism 2710 also supports a locking pin 2716. In various embodiments, the locking pin 2716 is spring-loaded or otherwise biased to extend outwardly from the slidable mounting mechanism 2710 to engage a locking slot in the locking body 2720 to prevent the locking body 2720 from sliding. The locking pin 2716 may be manually retracted away from the locking body 2720 to permit the locking body 2720 to be moved to an unlocked position.

In various embodiments, the slidable mounting mechanism 2710 includes a torque transfer mechanism to transfer torque between the electrosurgical instrument or device 118 (FIG. 1) and the user interface 102. In various embodiments, the torque transfer mechanism includes a linkage 2728 that is received within a channel 2718 when the locking body 2720 is in a locked position. The linkage 2728 and the channel 2718 thus transfer torque between the locking body 2720 that is engaged with the electrosurgical instrument or device 118 and the slidable sleeve 612. The linkage 2718 and channel 2728 thus absorb and/or transfer torque between the electrosurgical instrument or device 118 and the slidable sleeve 612, rather than, for example, the torque being exerted on the retaining ring 2730 and/or the locking pin 2716. In various embodiments, torque also may be absorbed and transferred by strengthening the locking pin 2716 and/or tightening and strengthening the mounting of the retaining ring 2730 to the lock plate 2720.

The locking body 2720 has a base plate 2722 configured to slide across the slidable mounting mechanism 2710 and to hold the flange 2754 in place within the slidable sleeve 612 to secure the user interface 102 to the electrosurgical device 118. As further described with reference to FIG. 28, the base plate 2722 defines an opening having differently-sized sections that alternately permit insertion of the flange 2754 into the slidable sleeve 612 and prevent removal of the flange 2754 from the slidable sleeve 612. The locking body 2720 supports a hood 2724 that extends over the combination formed by the surgical device interface 2752 with the user interface 102 via the slidable sleeve 612. As previously mentioned, the locking body 2720 also supports the second indicator tab 2728. The second indicator tab 2728 aligns with the first indicator tab 2718 on the slidable mounting mechanism 2710 when the locking body 2720 is in a locked position to provide visual confirmation when the locking body 2720 is in a locked position.

The locking body 2720 is slidably secured to the slidable mounting mechanism with a retainer ring 2730. The retainer ring 2730 includes a ring 2732 having an inner diameter 2799 that is sized to receive the flange 2754 extending from the surgical device interface 2752 therethrough. Extending from the ring 2732 are one or more retaining clips 2734. The retaining clips 2734 are sized to fit through slots in the base plate 2722 of the locking body, as further described below with reference to FIG. 28. Once the retaining clips 2734 are extended through the slots in the base plate 2722 of the locking body 2720, the retaining clips are secured onto and/or around the projections 2714 on the slidable mounting mechanism 2710. Once the retaining clips 2734 are extended through the slots on the locking body 2720 and secured onto the projections 2714 on the slidable locking mechanism 2710, the locking body 2720 is slidably constrained to move across the slidable mounting mechanism 2710 to lock and unlock the user interface 102 with the electrosurgical device 118.

Referring to FIG. 28, the base plate 2722 defines two retaining slots 2895 through which the retaining clips 2734 (FIG. 27) extend from the retaining ring 2730. The retaining slots 2895 are sized to slidably receive the retaining clips 2734 so that the locking body 2720 can slide in a first direction 2815 or a second direction 2817 across the retaining clips 2734. The ring 2732 of the retaining ring 2730 lies across the base plate 2722 to hold the locking body 2720 to the slidable mounting mechanism 2710 (FIG. 27). The locking body 2720 also supports at least one socket 2820 to receive the locking pin 2716 (FIG. 27) extending from the slidable locking mechanism 2710. The socket 2820 is positioned to engage the locking pin 2716 when the locking body 2720 is slid into a locked position over the surgical device interface 2752.

The hood 2724 extends from the locking plate 2722 to cover the connection between the surgical device interface 2752 and the user interface 102. To allow the locking body 2720 to move in the second direction 2817 without the hood 2724 being blocked by a body of the electrosurgical device 118 (FIG. 1), a lower edge 2825 of the hood 2724 is shaped to define a recess 2827. When the locking body 2720 is moved in the second direction 2817 to move the locking body 2720 into a locked position, the recess 2827 receives the body of the electrosurgical device 118.

The base plate 2722 of the locking body 2720 defines an opening 2810 through which, as described with reference to FIG. 27, the flange 2754 on the surgical device interface 2772 may be inserted into the slidable sleeve 612. More specifically, a first section 2801 of the opening has a first width 2811 and a conjoined second section 2803 with a second width 2813. The first width 2811 of the first section is large enough to receive the outer width 2793 of the flange 2754 therethrough, while the second width 2813 of the second section 2803 is large enough to receive the width 2795 of the surgical device interface 2752 but not to allow the outer width 2793 of the flange 2754 to pass therethrough.

To lock the user interface 102 with the electrosurgical device 118 (not shown in FIG. 28), the locking body 2720 is slid in the first direction 2815 to position the first section 2801 over the opening in the base portion 2712 of the slidable mounting mechanism 2710 that leads into the slidable sleeve 612 (not shown in FIG. 28). The flange 2754 that extends from the surgical device interface 2752 is then inserted through the first section 2801 and into the slidable sleeve 612. To secure the surgical device interface 2752 in place, the locking body is slid in the second direction 2817. As a result, the second section 2803 is moved over the opening in the base portion 2712 of the slidable mounting mechanism 2710, and an edge of the locking body 2722 slides over and abuts the flange 2754. In this locked position, the edge of the locking plate 2722 around the second section 2803 cover the flange 2754 and holds the flange 2754 in place. Also, with the locking body 2720 in this locked position, the locking pin 2716 extends into the socket 2820. The locking pin 2716 blocks movement of the locking plate in the first direction 2815 until the locking pin 2716 is withdrawn from the socket 2820.

To uncouple the user interface 102 from the electrosurgical device 118, a user engages the locking pin 2716 to slide it out of the socket 2820 to permit sliding movement of the locking body 2720. With the locking pin 2716 withdrawn, the locking body 2720 is slid in the first direction 2815 so that the base plate 2722 moves away from the surgical device interface 2752 with the first section 2801 of the opening 2810 over the flange 2752. The flange 2754 of the surgical device interface 2752 can now be withdrawn through the locking body 2720, ending the connection between the surgical device interface 2752 and the slidable sleeve 612 of the user interface 102.

Referring to FIG. 29, an illustrative method 2900 of positioning electrodes for treatment is provided. The method 2900 starts at a block 2905. At a block 2910, a distal end of a sheath that contains a primary electrode and a secondary electrode is moved adjacent to a target region, as described with reference to FIGS. 6A-7B. At a block 2920, a primary actuator, that is operably coupled with the primary electrode and a secondary actuator that is operably coupled to the secondary electrode and that is movably engaged with the primary actuator, is slid to a first position to motivate distal ends of the primary electrode and the secondary electrode relative to the target region, as described with reference to FIGS. 14A and 14B. At a block 2930, the secondary actuator is rotated relative to the primary actuator to cause the secondary actuator to travel independently of the primary actuator along a helical path to a second position to motivate the distal end of the secondary electrode to move independently of the primary electrode relative to the target region, as previously described with reference to FIGS. 16A and 16B. The method 2900 ends at a block 2935, with the electrodes now positioned.

Referring to FIG. 30, an illustrative method 3000 of motivating an implement through a helical path having a varied pitch is provided. The method 3000 starts at a block 3005. At a block 3010, an elongated implement is coupled at a proximal end thereof to an actuator that is movable along an axis, as described with reference to FIG. 11. At a block 3020, the implement is motivated by rotatably moving the actuator through a generally helical path around the axis, the helical path having a pitch that is varied to change a distance traveled by the actuator along the axis per unit of rotation of the actuator, as described with reference to FIGS. 16A, 16B, 22, and 23. The method 3000 ends at a block 3025, with the actuator having moved the implement.

Referring to FIG. 31, an illustrative method 3100 of securing devices together is provided. The method 3100 starts at a block 3105. At a block 3110, a locking body is positioned into an open position, where the locking body defines an opening with a first section having a first width and a second section having a second width that is smaller than the first width. The locking body is slidably mounted on one of a first device that supports a first coupling and a second device that supports a second coupling. The first section is disposed between the first coupling and the second coupling when the locking body is positioned into the open position, as described with reference to FIG. 28. At a block 3120, a connection is formed by inserting the first coupling within the second coupling where one of the first and second couplings supports a flange having a flange width that is smaller than the first width and larger than the second width, as described with reference to FIG. 28. At a block 3130, the locking body is repositioned into a closed position in which an edge of the locking body around the second section abuts the flange so that the coupling that supports the flange is prevented from being withdrawn from the connection, as previously described with reference to FIG. 28. The method 3100 ends at a block 3135, with the couplings secured together by the locking body.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    a locking body including intersecting bores that define an opening in the locking body with a first bore having a first diameter and a second bore having a second diameter that is smaller than the first diameter the second bore intersecting the first bore, the locking body being slidably mountable for linear movement on one of a first device that supports a first coupling and a second device that supports a second coupling, one of the first and second couplings being configured to support thereon a flange having a flange diameter that is smaller than the first diameter and larger than the second diameter; and
    a slidable mounting mechanism configured to slidably secure the locking body on one of the first device and the second device, the slidable mounting mechanism being further configured to enable the locking body to linearly slide between an open position, in which the first bore is positionable to enable the first coupling to be inserted into the second coupling to form a connection, and a closed position in which an edge of the locking body around at least a portion of a perimeter of the second bore abuts the flange such that the coupling that supports the flange is prevented from being withdrawn from the connection.

2. The apparatus of claim 1, further comprising a latch mechanism configured to engage the locking body that is positioned in the closed position such that the locking body is prevented from sliding without the latch mechanism being disengaged from the locking body.

3. The apparatus of claim 2, further comprising a biasing mechanism that is configured to urge the latch mechanism into a locked position to prevent the locking body from sliding from the closed position.

4. The apparatus of claim 2, wherein the latch mechanism includes a locking pin that is at least partially insertable into the locking body that is positioned in the closed position.

5. The apparatus of claim 2, wherein the latch mechanism is mounted on the slidable mounting mechanism.

6. The apparatus of claim 2, wherein each of the locking body and the slidable mounting mechanism includes at least one indicator tab, the at least one indicator tab disposed on the locking body being alignable with the at least one indicator tab disposed on the slidable mounting mechanism, the at least one indicator tab disposed on the locking body and the at least one indicator tab disposed on the slidable mounting mechanism being configured to provide a visual indication to a user responsive to engagement of the locking body by the latch mechanism.

7. The apparatus of claim 1, wherein the slidable mounting mechanism includes:
    a base portion coupled to the one of the first device and the second device, wherein the base portion abuts a first face of the locking body; and
    a retaining ring configured to engage a second face of the locking body, wherein the retaining ring includes at least one retaining member configured to engage the base portion to slidably retain the locking body against the base portion.

8. The apparatus of claim 1, further comprising a hood that extends over the connection of the first coupling and the second coupling.

9. The apparatus of claim 8, wherein the hood is contoured to permit the locking body to slide between the open position and the closed position without impacting the first device and the second device.

10. A system comprising:
    an elongated primary electrode defining a lumen therein;
    an elongated secondary electrode slidably received within the lumen;
    a sheath slidably receiving the primary electrode and being configured to convey the primary electrode and the secondary electrode toward a target region;
    a housing operably coupled with the sheath and movably mounted to slidably motivate the sheath relative to the target region;
    a primary actuator operably coupled with the primary electrode and movably coupled with the housing to motivate the primary electrode relative to the sheath;
    a secondary actuator operably coupled with the secondary electrode and movably coupled with the primary actuator, wherein the secondary actuator is separately movable relative to the primary actuator to motivate the secondary electrode to move relative to the primary electrode;
    a first coupling supported by the housing and configured to engage a second coupling supporting a flange having a flange diameter, wherein the second coupling extends from a device through which the sheath and the electrodes will be conveyed to the target region;
    a locking body including intersecting circular bores that define an opening in the locking body having a first section having a first diameter larger than the flange diameter and a second section having a second diameter that is smaller than the flange diameter, the locking body being slidably mountable for linear movement; and
    a slidable mounting mechanism configured to slidably secure the locking body to the housing, the slidable mounting mechanism being further configured to enable the locking body to linearly slide between an open position, in which the first section is positionable to enable the first coupling to insertably receive the second coupling to form a connection, and a closed position in which an edge of the locking body around the second section abuts the flange such that the coupling that supports the flange is prevented from being withdrawn from the connection, wherein the slidable mounting mechanism slides between the open position and the closed position in a direction transverse to a longitudinal axis of the housing.

11. The system of claim 10, further comprising a latch mechanism configured to engage the locking body that is positioned in the closed position such that the locking body is prevented from sliding without the latch mechanism being disengaged from the locking body.

12. The system of claim 11, further comprising a biased mechanism that is configured to urge the latch mechanism in a locked position to prevent the locking body from sliding from the closed position.

13. The system of claim 12, wherein the latch mechanism includes a locking pin that is at least partially insertable into the locking body that is positioned in the closed position.

14. The system of claim 11, wherein the latch mechanism is mounted on the slidable mounting.

15. The system of claim 11, wherein each of the locking body and the slidable mounting mechanism includes at least one indicator tab, the at least one indicator tab disposed on the locking body being alignable with the at least one indicator tab disposed on the slidable mounting, the at least one indicator tab disposed on the locking body and the at least one indicator tab disposed on the slidable mounting mechanism being configured to provide a visual indication to a user responsive to engagement of the locking body by the latch mechanism.

16. The system of claim 10, wherein the slidable mounting mechanism includes:
a base portion coupled to the one of the first device and the second device, wherein the base portion abuts a first face of the locking body; and
a retaining clip configured to engage a second face of the locking body, wherein the retaining clip includes at least one retaining member configured to engage the base portion to slidably retain the locking body against the base portion.

17. The system of claim 10, further comprising a hood that extends over the connection of the first coupling and the second coupling.

18. The system of claim 17, wherein the hood is contoured to permit the locking body to slide between the open position and the closed position without impacting the first device and the second device.

19. A method comprising:
positioning a locking body into an open position, the locking body defining an opening formed by intersecting bores a first bore of the intersecting bores having a first diameter and a second bore of the intersecting bores having a second diameter that is smaller than the first diameter, the locking body being slidably mounted for linear movement on one of a first device that supports a first coupling and a second device that supports a second coupling, the first bore being disposed between the first coupling and the second coupling when the locking body is positioned into the open position;
forming a connection by inserting the first coupling within the second coupling such that one of the first and second couplings supports a flange having a flange diameter that is smaller than the first diameter and larger than the second diameter; and
sliding, linearly, the locking body into a closed position in which an edge of the locking body around the second bore abuts the flange such that prevent the coupling that supports the flange is prevented from being withdrawn from the connection.

20. The method of claim 19, further comprising locking the locking body in place to prevent movement of the locking body after the locking body is moved into the closed position.

21. The apparatus of claim 1, wherein the first bore defines a first semi-circular cutout portion conjoined with the second bore that defines a second semi-circular cutout portion.

22. The apparatus of claim 1, wherein the slidable mounting mechanism is configured to enable the locking body to slide, between the open position and the closed position, transversely to a longitudinal axis of the apparatus.

* * * * *